(12) United States Patent
Yukawa et al.

US009290770B2

(10) Patent No.: US 9,290,770 B2
(45) Date of Patent: Mar. 22, 2016

(54) CORYNEFORM BACTERIUM TRANSFORMANT AND PROCESS FOR PRODUCING VALINE USING THE SAME

(75) Inventors: Hideaki Yukawa, Kyoto (JP); Masayuki Inui, Kyoto (JP)

(73) Assignee: RESEARCH INSTITUTE OF INNOVATIVE TECHNOLOGY FOR THE EARTH, Kyoto (JP)

( * ) Notice: Subject to any disclaimer, the term of this patent is extended or adjusted under 35 U.S.C. 154(b) by 0 days.

(21) Appl. No.: 14/238,527

(22) PCT Filed: Aug. 21, 2012

(86) PCT No.: PCT/JP2012/071019
§ 371 (c)(1),
(2), (4) Date: Apr. 16, 2014

(87) PCT Pub. No.: WO2013/027709
PCT Pub. Date: Feb. 28, 2013

(65) Prior Publication Data
US 2014/0227747 A1 Aug. 14, 2014

(30) Foreign Application Priority Data
Aug. 22, 2011 (JP) .................. 2011-180898

(51) Int. Cl.
*C12N 15/77* (2006.01)
*C12P 13/08* (2006.01)
*C12N 9/04* (2006.01)
*C12N 9/06* (2006.01)
*C12N 9/10* (2006.01)

(52) U.S. Cl.
CPC .............. *C12N 15/77* (2013.01); *C12N 9/0006* (2013.01); *C12N 9/0016* (2013.01); *C12N 9/1022* (2013.01); *C12P 13/08* (2013.01); *C12Y 101/01086* (2013.01); *C12Y 104/01009* (2013.01); *C12Y 202/01006* (2013.01); *Y02P 20/52* (2015.11)

(58) Field of Classification Search
None
See application file for complete search history.

(56) References Cited

U.S. PATENT DOCUMENTS

| 7,632,663 B1 | 12/2009 | Eggeling et al. |
| 2008/0153139 A1 | 6/2008 | Marienhagen et al. |
| 2009/0053779 A1 | 2/2009 | Lee et al. |
| 2009/0087885 A1 | 4/2009 | Groeger et al. |

FOREIGN PATENT DOCUMENTS

| CN | 102286505 A | 12/2011 |
| JP | H05344893 A | 12/1993 |
| JP | 2002-537771 A | 11/2002 |
| JP | 2005245466 A | 9/2005 |
| JP | 2007-043947 A | 2/2007 |
| JP | 2007529234 A | 10/2007 |
| JP | 2008-514191 A | 5/2008 |
| JP | 2009-521960 A | 6/2009 |
| WO | WO-2010113832 A1 | 10/2010 |
| WO | WO-2012061653 A2 | 5/2012 |

OTHER PUBLICATIONS

Park et al. Biotechnology and Bioengineering (May 2011) 108 (5) 1140-1147.*
Krause et al. Appl. Environm. Microbiol. (Dec. 2010) 76 (24) 8053-8061.*
International Preliminary Report on Patentability in corresponding PCT/JP2012/071019 dated Feb. 25, 2014. (English Translation).
International Search Report in corresponding PCT/JP2012/071019 dated Nov. 6, 2012.
Written Opinion in corresponding PCT/JP2012/071019 dated Nov. 6, 2012.
Blombach, "Corynebacterium glutamicum tailored for high-yield L-valine production," *Appl Microbiol Biotechnol*, vol. 79, pp. 471-479 (2008).
Elisakova et al., "Feedback-Resistant Acetohydroxy Acid Synthase Increases Valine Production in Corynebacterium Glutamicum," *Applied and Environmental Microbiology*, pp. 207-213 (2005).
Holatko et al., "Metabolic engineering of the L-valine biosynthesis pathway is Corynebacterium Glutamicum Using Promoter Activity Modulation," *Journal of Biotechnology*, vol. 139, pp. 203-210 (2009).
Leyval et al., "Characterisation of the Enzyme Activities Involved in the Valine Biosynthetic Pathway in a Valine-producing Strain of Corynebacterium Glutamicum," *Journal of Biotechnology*, vol. 104, pp. 241-252 (2003).
Extended European Search Report in corresponding PCT/JP2012/071019 dated Mar. 24, 2015.
Yamamoto et al., "Diversity of metabolic shift in response to oxygen deprivation in Corynebacterium glutamicum and its close relatives", *Appl Microbiol Biotechnol*, (2011) 90:1051-1061.
Hasegawa et al. "Improvement of the Redox Balance Increases $_L$-Valine Production by Corynebacterium glutamicum under Oxygen Deprivation Conditions", *Application and Environmental Microbiology*, vol. 78, No. 3, pp. 865-875 (2012).

(Continued)

*Primary Examiner* — Nashaat Nashed
(74) *Attorney, Agent, or Firm* — Marshall, Gerstein & Borun LLP

(57) ABSTRACT

A transformant obtainable by introducing one or more of the following DNAs (a), (b), and (c) into a coryneform bacterium as a host.
(a) A DNA which encodes acetohydroxy acid synthase derived from *Corynebacterium glutamicum* and which has a mutation changing the glycine at position 156 to glutamic acid (G156E) in an amino acid sequence encoded by the DNA, or an analog thereof.
(b) A DNA which encodes acetohydroxy acid isomeroreductase derived from *Corynebacterium glutamicum* and which has mutations changing the serine at position 34 to glycine (S34G), the leucine at position 48 to glutamic acid (L48E), and the arginine at position 49 to phenylalanine (R49F) in an amino acid sequence encoded by the DNA, or an analog thereof.
(c) A DNA which encodes leucine dehydrogenase derived from *Lysinibacillus sphaericus*, or an analog thereof.

6 Claims, 2 Drawing Sheets

(56) References Cited

OTHER PUBLICATIONS

Satoshi Hasegawa, et al., "Efficient Valine Production Using Coryneform Bacterium Under Reducing Conditions", Annual Meeting of Japan Society of Bioscience, Biotechnology and Agrochemistry 2010, p. 203. (English Translation).

Toshihisa Ohshima, et al., "Properties of Crystalline Leucine Dehydrogenase from Bacillus sphaericus", J. Biol. Chem., vol. 253, No. 16, pp. 5719-5725 (1978).

Reina Katoh et al., "Cloning and sequencing of the leucine dehydrogenase gene from Bacillus sphaericus IFO 3525 and importance of the C-terminal region for the enzyme activity", Journal of Molecular Catalysis B: Enzymatic, vol. 23, pp. 239-247 (2003).

* cited by examiner

SEQUENCE LISTING

<160> NUMBER OF SEQ ID NOS: 57

<210> SEQ ID NO 1
<211> LENGTH: 1195
<212> TYPE: DNA
<213> ORGANISM: Corynebacterium casei

<400> SEQUENCE: 1

```
atgaaaaccg accgtgcacg ctcgtgtgag aaagtcagct acatgagacc aactacccgc        60
cctgagggac gcttttgagca gctgtggctg ccgctgtggc cattggcaag cgatgacctc       120
cgtgagggca tttaccgcac ctcacggaag aacgcgctgg ataagcgcta cgtcgaagcc       180
aatcccgacg cgctctctaa cctcctggtc gttgacatcg accaggagga cgcgcttttg       240
cgctctttgt gggacaggga ggactggaga cctaacgcgg tggttgaaaa cccccttaaac      300 gggcacgcac acgctgtctg ggcgctcgcg gagccattta cccgcaccga atacgccaaa       360
cgcaagcctt tggcctatgc cgcggctgtc accgaaggcc tacggcgctc tgtcgatggc       420
gatagcggat actccgggct gatcaccaaa aaccccgagc acactgcatg ggatagtcac       480
tggatcaccg ataagctgta tacgctcgat gagctgcgct tttggctcga agaaaccggc       540
tttatgccgc ctgcgtcctg gaggaaaacg cggcggttct cgccagttgg tctaggtcgt       600
aattgcgcac tcttttgaaag cgcacgtacg tgggcatatc gggaggtcag aaagcatttt    660
ggagacgctg acggcctagg ccgcgcaatc caaaccaccg cgcaagcact taaccaagag      720
```

| | |
|---|---|
| ctgtttgatg aaccactacc tgtggccgaa gttgactgta ttgccaggtc aatccataaa | 780 |
| tggatcatca ccaagtcacg catgtggaca gacggcgccg ccgtctacga cgccacattc | 840 |
| accgcaatgc aatccgcacg cgggaagaaa ggctggcaac gaagcgctga ggtgcgtcgt | 900 |
| gaggctggac atactctttg gaggaacatt ggctaaggtt tatgcacgtt atccacgcaa | 960 |
| cggaaaaaca gcccgcgagc tgcagaacg tgccggtatg tcggtgagaa cagctcaacg | 1020 |
| atggacttcc gaaccgcgtg aagtgttcat taaacgtgcc aacgagaagc gtgctcgcgt | 1080 |
| ccaggagctg cgcgccaaag gtctgtccat gcgcgctatc gcggcagaga ttggttgctc | 1140 |
| ggtgggcacg gttcaccgct acgtcaaaga agttgaagag aagaaaaccg cgtaa | 1195 |

<210> SEQ ID NO 2
<211> LENGTH: 2227
<212> TYPE: DNA
<213> ORGANISM: Artificial sequence
<220> FEATURE:
<223> OTHER INFORMATION: pHSG398

<400> SEQUENCE: 2

| | |
|---|---|
| acggaagatc acttcgcaga ataaataaat cctggtgtcc ctgttgatac cgggaagccc | 60 |
| tgggccaact tttggcgaaa atgagacgtt gatcggcacg taagaggttc aactttcac | 120 |
| cataatgaaa taagatcact accgggcgta ttttttgagt tatcgagatt ttcaggagct | 180 |
| aaggaagcta aaatggagaa aaaaatcact ggatatacca ccgttgatat atcccaatgg | 240 |
| catcgtaaag aacatttga ggcatttcag tcagttgctc aatgtaccta taaccagacc | 300 |
| gttcagctgg atattacggc ctttttaaag accgtaaaga aaaataagca caagttttat | 360 |
| ccggccttta ttcacattct tgcccgcctg atgaatgctc atccggaatt cgtatggca | 420 |
| atgaaagacg gtgagctggt gatatgggat agtgttcacc cttgttacac cgttttccat | 480 |
| gagcaaactg aaacgttttc atcgctctgg agtgaatacc acgacgattt ccggcagttt | 540 |
| ctacacatat attcgcaaga tgtggcgtgt tacggtgaaa acctggccta tttccctaaa | 600 |
| gggtttattg agaatatgtt tttcgtctca gccaatccct gggtgagttt caccagtttt | 660 |
| gatttaaacg tggccaatat ggacaacttc ttcgccccg ttttcaccat gggcaaatat | 720 |
| tatacgcaag gcgacaaggt gctgatgccg ctggcgattc aggttcatca tgccgtctgt | 780 |
| gatggcttcc atgtcggcag aatgcttaat gaattacaac agtactgcga tgagtggcag | 840 |
| ggcggggcgt aatttttta aggcagttat tggtgccctt aaacgcctgg tgctacgcct | 900 |
| gaataagtga taataagcgg atgaatggca gaaattcagc ttggcccagt gccaagctcc | 960 |
| aatacgcaaa ccgcctctcc ccgcgcgttg gccgattcat taatgcagct ggcacgacag | 1020 |
| gtttcccgac tggaaagcgg gcagtgagcg caacgcaatt aatgtgagtt agctcactca | 1080 |
| ttaggcaccc caggctttac actttatgct tccggctcgt atgttgtgtg gaattgtgag | 1140 |
| cggataacaa tttcacacag gaaacagcta tgaccatgat tacgaattcg agctcggtac | 1200 |
| ccggggatcc tctagagtcg acctgcaggc atgcaagctt ggcactggcc gtcgttttac | 1260 |
| aacgtcgtga ctgggaaaac cctggcgtta cccaacttaa tcgccttgca gcacatcccc | 1320 |
| ctttcgccag ctggcgtaat agcgaagagg cccgcaccga tcgcccttcc caacagttgc | 1380 |
| gcagcctgaa tggcgaatga gcttcttccg cttcctcgct cactgactcg ctgcgctcgg | 1440 |
| tcgttcggct gcggcgagcg gtatcagctc actcaaaggc ggtaatacgg ttatccacag | 1500 |
| aatcagggga taacgcagga agaacatgt gagcaaaagg ccagcaaaag gccaggaacc | 1560 |
| gtaaaaaggc cgcgttgctg gcgtttttcc ataggctccg cccccctgac gagcatcaca | 1620 |

-continued

```
aaaatcgacg ctcaagtcag aggtggcgaa acccgacagg actataaaga taccaggcgt    1680 ttcccctgg aagctccctc gtgcgctctc ctgttccgac cctgccgctt accggatacc    1740
tgtccgcctt tctcccttcg ggaagcgtgg cgctttctca atgctcacgc tgtaggtatc    1800
tcagttcggt gtaggtcgtt cgctccaagc tgggctgtgt gcacgaaccc cccgttcagc    1860
ccgaccgctg cgccttatcc ggtaactatc gtcttgagtc caacccggta agacacgact    1920
tatcgccact ggcagcagcc actggtaaca ggattagcag agcgaggtat gtaggcggtg    1980
ctacagagtt cttgaagtgg tggcctaact acggctacac tagaaggaca gtatttggta    2040
tctgcgctct gctgaagcca gttaccttcg gaaaaagagt tggtagctct tgatccggca    2100
aacaaaccac cgctggtagc ggtggttttt tgtttgcaa gcagcagatt acgcgcagaa    2160
aaaaaggatc tcaagaagat cctttgatct tttctacggg gtctgacgct cagtggaact    2220
ccgtcga                                                              2227

<210> SEQ ID NO 3
<211> LENGTH: 24
<212> TYPE: DNA
<213> ORGANISM: Artificial sequence
<220> FEATURE:
<223> OTHER INFORMATION: PCR primer

<400> SEQUENCE: 3
ggcagagatc tagaacgtcc gtag                                             24

<210> SEQ ID NO 4
<211> LENGTH: 26
<212> TYPE: DNA
<213> ORGANISM: Artificial sequence
<220> FEATURE:
<223> OTHER INFORMATION: PCR primer

<400> SEQUENCE: 4
cggaaagatc tgacttggtt acgatg                                           26

<210> SEQ ID NO 5
<211> LENGTH: 24
<212> TYPE: DNA
<213> ORGANISM: Artificial sequence
<220> FEATURE:
<223> OTHER INFORMATION: PCR primer

<400> SEQUENCE: 5
cagtggagat ctgtcgaacg gaag                                             24

<210> SEQ ID NO 6
<211> LENGTH: 24
<212> TYPE: DNA
<213> ORGANISM: Artificial sequence
<220> FEATURE:
<223> OTHER INFORMATION: PCR primer

<400> SEQUENCE: 6
ccgttagatc tagttccact gagc                                             24

<210> SEQ ID NO 7
<211> LENGTH: 1195
<212> TYPE: DNA
<213> ORGANISM: Corynebacterium casei

<400> SEQUENCE: 7
```

```
atgaaaaccg accgtgcacg ctcgtgtgag aaagtcagct acatgagacc aactacccgc    60
cctgagggac gctttgagca gctgtggctg ccgctgtggc cattggcaag cgatgacctc   120
cgtgagggca tttaccgcac ctcacggaag aacgcgctgg ataagcgcta cgtcgaagcc   180
aatcccgacg cgctctctaa cctcctggtc gttgacatcg accaggagga cgcgcttttg   240
cgctctttgt gggacaggga ggactggaga cctaacgcgg tggttgaaaa ccccttaaac   300
gggcacgcac acgctgtctg gcgctcgcg gagccattta cccgcaccga atacgccaaa   360
cgcaagcctt tggcctatgc cgcggctgtc accgaaggcc tacggcgctc tgtcgatggc   420
gatagcggat actccgggct gatcaccaaa accccgagc acactgcatg ggatagtcac   480
tggatcaccg ataagctgta tacgctcgat gagctgcgct tttggctcga agaaaccggc   540
tttatgccgc ctgcgtcctg gaggaaaacg cggcggttct cgccagttgg tctaggtcgt   600
aattgcgcac tctttgaaag cgcacgtacg tgggcatatc gggaggtcag aaagcatttt   660
ggagacgctg acggcctagg ccgcgcaatc caaaccaccg cgcaagcact taaccaagag   720
ctgtttgatg aaccactacc tgtggccgaa gttgactgta ttgccaggtc aatccataaa   780
tggatcatca ccaagtcacg catgtggaca gacggcgccg ccgtctacga cgccacattc   840
accgcaatgc aatccgcacg cgggaagaaa ggctggcaac gaagcgctga ggtgcgtcgt   900
gaggctggac atactctttg gaggaacatt ggctaaggtt tatgcacgtt atccacgcaa   960
cggaaaaaca gcccgcgagc tggcagaacg tgccggtatg tcggtgagaa cagctcaacg  1020
atggacttcc gaaccgcgtg aagtgttcat taaacgtgcc aacgagaagc gtgctcgcgt  1080
ccaggagctg cgcgccaaag gtctgtccat gcgcgctatc gcggcagaga ttggttgctc  1140
ggtgggcacg gttcaccgct acgtcaaaga agttgaagag aagaaaaccg cgtaa        1195
```

<210> SEQ ID NO 8
<211> LENGTH: 2675
<212> TYPE: DNA
<213> ORGANISM: Artificial sequence
<220> FEATURE:
<223> OTHER INFORMATION: pHSG298

<400> SEQUENCE: 8

```
gaggtctgcc tcgtgaagaa ggtgttgctg actcatacca ggcctgaatc gccccatcat    60
ccagccagaa agtgagggag ccacggttga tgagagcttt gttgtaggtg gaccagttgg   120
tgattttgaa cttttgcttt gccacggaac ggtctgcgtt gtcgggaaga tgcgtgatct   180
gatccttcaa ctcagcaaaa gttcgattta ttcaacaaag ccacgttgtg tctcaaaatc   240
tctgatgtta cattgcacaa gataaaaata tatcatcatg aacaataaaa ctgtctgctt   300
acataaacag taatacaagg ggtgttatga gccatattca acgggaaacg tcttgctcga   360
agccgcgatt aaattccaac atggatgctg atttatatgg gtataaatgg gctcgcgata   420
atgtcgggca atcaggtgcg acaatctatc gattgtatgg gaagcccgat gcgccagagt   480
tgtttctgaa acatggcaaa ggtagcgttg ccaatgatgt tacagatgag atggtcagac   540
taaactggct gacggaattt atgcctcttc cgaccatcaa gcattttatc cgtactcctg   600
atgatgcatg gttactcacc actgcgatcc ccgggaaaac agcattccag gtattagaag   660
aatatcctga ttcaggtgaa aatattgttg atgcgctggc agtgttcctg cgccggttgc   720
attcgattcc tgtttgtaat tgtccttttta acagcgatcg cgtatttcgt ctcgctcagg   780
cgcaatcacg aatgaataac ggtttggttg atgcgagtga ttttgatgac gagcgtaatg   840
gctggcctgt tgaacaagtc tggaaagaaa tgcataagct tttgccattc tcaccggatt   900
```

```
cagtcgtcac tcatggtgat ttctcacttg ataaccttat ttttgacgag gggaaattaa     960
taggttgtat tgatgttgga cgagtcggaa tcgcagaccg ataccaggat cttgccatcc    1020
tatggaactg cctcggtgag ttttctcctt cattacagaa acggcttttt caaaaatatg    1080
gtattgataa tcctgatatg aataaattgc agtttcattt gatgctcgat gagttttct    1140 aatcagaatt ggttaattgg ttgtaacact ggcagagcat tacgctgact tgacgggacg    1200
gcggctttgt tgaataaatc gcattcgcca ttcaggctgc gcaactgttg gaagggcga    1260 tcggtgcggg cctcttcgct attacgccag ctggcgaaag ggggatgtgc tgcaaggcga    1320
ttaagttggg taacgccagg gttttcccag tcacgacgtt gtaaaacgac ggccagtgcc    1380
aagcttgcat gcctgcaggt cgactctaga ggatccccgg gtaccgagct cgaattcgta    1440
atcatgtcat agctgtttcc tgtgtgaaat tgttatccgc tcacaattcc acacaacata    1500
cgagccggaa gcataaagtg taaagcctgg ggtgcctaat gagtgagcta actcacatta    1560
attgcgttgc gctcactgcc cgcttttcag tcgggaaacc tgtcgtgcca gctgcattaa    1620
tgaatcggcc aacgcgcggg gagaggcggt ttgcgtattg gcgacttttt gctgagttga    1680
aggatcagat cacgcatctt cccgacaacg cagaccgttc cgtggcaaag caaaagttca    1740
aaatcagtaa ccgtcagtgc cgataagttc aaagttaaac ctggtgttga taccaacatt    1800
gaaacgctga tcgaaaacgc gctgaaaaac gctgctgaat gtgcgagctt cttccgcttc    1860
ctcgctcact gactcgctgc gctcggtcgt tcggctgcgg cgagcggtat cagctcactc    1920
aaaggcggta atacggttat ccacagaatc aggggataac gcaggaaaga acatgtgagc    1980
aaaaggccag caaaaggcca ggaaccgtaa aaaggccgcg ttgctggcgt ttttccatag    2040
gctccgcccc cctgacgagc atcacaaaaa tcgacgctca agtcagaggt ggcgaaaccc    2100
gacaggacta taaagatacc aggcgtttcc ccctggaagc tccctcgtgc gctctcctgt    2160
tccgaccctg ccgcttaccg gatacctgtc cgcctttctc ccttcgggaa gcgtggcgct    2220
ttctcaatgc tcacgctgta ggtatctcag ttcggtgtag tcgttcgct ccaagctggg    2280 ctgtgtgcac gaaccccccg ttcagcccga ccgctgcgcc ttatccggta actatcgtct    2340
tgagtccaac ccggtaagac acgacttatc gccactggca gcagccactg gtaacaggat    2400
tagcagagcg aggtatgtag gcggtgctac agagttcttg aagtggtggc ctaactacgg    2460
ctacactaga aggacagtat ttggtatctg cgctctgctg aagccagtta ccttcggaaa    2520
aagagttggt agctcttgat ccggcaaaca aaccaccgct ggtagcggtg gtttttttgt    2580
ttgcaagcag cagattacgc gcagaaaaaa aggatctcaa gaagatcctt tgatcttttc    2640
tacggggtct gacgctcagt ggaacgatcc gtcga                                2675
```

<210> SEQ ID NO 9
<211> LENGTH: 24
<212> TYPE: DNA
<213> ORGANISM: Artificial sequence
<220> FEATURE:
<223> OTHER INFORMATION: PCR primer

<400> SEQUENCE: 9
ggcagagatc tagaacgtcc gtag                                              24

<210> SEQ ID NO 10
<211> LENGTH: 26
<212> TYPE: DNA
<213> ORGANISM: Artificial sequence
<220> FEATURE:

```
<223> OTHER INFORMATION: PCR primer

<400> SEQUENCE: 10
cggaaagatc tgacttggtt acgatg                                           26

<210> SEQ ID NO 11
<211> LENGTH: 23
<212> TYPE: DNA
<213> ORGANISM: Artificial sequence
<220> FEATURE:
<223> OTHER INFORMATION: PCR primer

<400> SEQUENCE: 11
gctggagatc taggtttccc gac                                              23

<210> SEQ ID NO 12
<211> LENGTH: 23
<212> TYPE: DNA
<213> ORGANISM: Artificial sequence
<220> FEATURE:
<223> OTHER INFORMATION: PCR primer

<400> SEQUENCE: 12
gggaaagatc tcgtgccagc tgc                                              23

<210> SEQ ID NO 13
<211> LENGTH: 1885
<212> TYPE: DNA
<213> ORGANISM: Corynebacterium glutamicum

<400> SEQUENCE: 13
agcatggtcg tcacagagct ggaagcggca gcgagaatta ccgcgatcg tggcgcggtg      60 cccgcaggca tgacaaacat cgtaaatgcc gcgtttcgtg tggccgtggc cgcccaggac    120
gtgtcagcgc cgccaccacc tgcaccgaat cggcagcagc gtcgcgcgtc gaaaaagcgc    180
acaggcggca agaagcgata agctgcacga atacctgaaa aatgttgaac gccccgtgag    240
cggtaactca cagggcgtcg gctaaccccc agtccaaacc tgggagaaag cgctcaaaaa    300
tgactctagc ggattcacga gacattgaca caccggcctg gaaatttcc gctgatctgt     360 tcgacaccca tcccgagctc gcgctgcgat cacgtggctg gacgagcgaa gaccgccgcg    420
aattcctcgc tcacctgggc agagaaaatt tccaggcag caagacccgc gacttcgcca     480
gcgcttggat caaagacccg gacacgggag aaacacagcc gaagttatac cgagttggtt    540
caaaatcgct tgcccggtgc cagtatgttg ctctgacgca cgcgcagcac gcagccgtgc    600
ttgtcctgga cattgatgtg ccgagccacc aggccggcgg gaaaatcgag cacgtaaacc    660
ccgaggtcta cgcgattttg gagcgctggg cacgcctgga aaaagcgcca gcttggatcg    720
gcgtgaatcc actgagcggg aaatgccagc tcatctggct cattgatccg gtgtatgccg    780
cagcaggcat gagcagcccg aatatgcgcc tgctggctgc aacgaccgag gaaatgaccc    840
gcgttttcgg cgctgaccag gcttttttcac ataggctgag ccggtggcca ctgcacgtct    900
ccgacgatcc caccgcgtac cgctggcatg cccagcacaa tcgcgtggat cgcctagctg    960
atcttatgga ggttgctcgc atgatctcag gcacagaaaa acctaaaaaa cgctatgagc   1020
aggagttttc tagcggacgg gcacgtatcg aagcggcaag aaaagccact gcggaagcaa   1080
aagcacttgc cacgcttgaa gcaagcctgc cgagcgccgc tgaagcgtct ggagagctga   1140
tcgacggcgt ccgtgtcctc tggactgctc cagggcgtgc cgcccgtgat gagacggctt   1200
ttcgccacgc tttgactgtg ggataccagt taaaagcggc tggtgagcgc ctaaaagaca   1260
```

-continued

```
ccaagatcat cgacgcctac gagcgtgcct acaccgtcgc tcaggcggtc ggagcagacg    1320
gccgtgagcc tgatctgccg ccgatgcgtg accgccagac gatggcgcga cgtgtgcgcg    1380
gctacgtcgc taaaggccag ccagtcgtcc ctgctcgtca gacagagacg cagagcagcc    1440
gagggcgaaa agctctggcc actatgggaa gacgtggcgg taaaaaggcc gcagaacgct    1500
ggaaagaccc aaacagtgag tacgcccgag cacagcgaga aaaactagct aagtccagtc    1560
aacgacaagc taggaaagct aaaggaaatc gcttgaccat tgcaggttgg tttatgactg    1620
ttgagggaga gactggctcg tggccgacaa tcaatgaagc tatgtctgaa tttagcgtgt    1680
cacgtcagac cgtgaataga gcacttaagt ctgcgggcat tgaacttcca cgaggacgcc    1740
gtaaagcttc ccagtaaatg tgccatctcg taggcagaaa acggttcccc ccgtaggggt    1800
ctctctcttg gcctcctttc taggtcgggc tgattgctct tgaagctctc tagggggget    1860 cacaccatag gcagataacg gttcc                                          1885

<210> SEQ ID NO 14
<211> LENGTH: 2675
<212> TYPE: DNA
<213> ORGANISM: Artificial sequence
<220> FEATURE:
<223> OTHER INFORMATION: pHSG298

<400> SEQUENCE: 14
gaggtctgcc tcgtgaagaa ggtgttgctg actcatacca ggcctgaatc gccccatcat      60
ccagccagaa agtgagggag ccacggttga tgagagcttt gttgtaggtg gaccagttgg     120
tgattttgaa cttttgcttt gccacggaac ggtctgcgtt gtcgggaaga tgcgtgatct     180
gatccttcaa ctcagcaaaa gttcgattta ttcaacaaag ccacgttgtg tctcaaaatc     240
tctgatgtta cattgcacaa gataaaaata tatcatcatg aacaataaaa ctgtctgctt     300
acataaacag taatacaagg ggtgttatga gccatattca acgggaaacg tcttgctcga     360
agccgcgatt aaattccaac atggatgctg atttatatgg gtataaatgg gctcgcgata     420
atgtcgggca atcaggtgcg acaatctatc gattgtatgg gaagcccgat gcgccagagt     480
tgtttctgaa acatggcaaa ggtagcgttg ccaatgatgt tacagatgag atggtcagac     540
taaactggct gacggaattt atgcctcttc cgaccatcaa gcattttatc cgtactcctg     600
atgatgcatg gttactcacc actgcgatcc ccgggaaaac agcattccag gtattagaag     660
aatatcctga ttcaggtgaa aatattgttg atgcgctggc agtgttcctg cgccggttgc     720
attcgattcc tgtttgtaat tgtcctttta acagcgatcg cgtatttcgt ctcgctcagg     780
cgcaatcacg aatgaataac ggtttggttg atgcgagtga ttttgatgac gagcgtaatg     840
gctggcctgt gaacaagtc tggaaagaaa tgcataagct tttgccattc tcaccggatt     900
cagtcgtcac tcatggtgat ttctcacttg ataaccttat ttttgacgag gggaaattaa     960
taggttgtat tgatgttgga cgagtcggaa tcgcagaccg ataccaggat cttgccatcc    1020
tatggaactg cctcggtgag ttttctcctt cattacagaa acggcttttt caaaaatatg    1080
gtattgataa tcctgatatg aataaattgc agtttcattt gatgctcgat gagtttttct    1140
aatcagaatt ggttaattgg ttgtaacact ggcagagcat tacgctgact tgacgggacg    1200
gcggctttgt tgaataaatc gcattcgcca ttcaggctgc gcaactgttg ggaagggcga    1260
tcggtgcggg cctcttcgct attacgccag ctggcgaaag gggatgtgc tgcaaggcga    1320 ttaagttggg taacgccagg gttttcccag tcacgacgtt gtaaaacgac ggccagtgcc    1380
```

```
aagcttgcat gcctgcaggt cgactctaga ggatccccgg gtaccgagct cgaattcgta    1440
atcatgtcat agctgtttcc tgtgtgaaat tgttatccgc tcacaattcc acacaacata    1500
cgagccggaa gcataaagtg taaagcctgg ggtgcctaat gagtgagcta actcacatta    1560
attgcgttgc gctcactgcc cgctttccag tcgggaaacc tgtcgtgcca gctgcattaa    1620
tgaatcggcc aacgcgcggg gagaggcggt ttgcgtattg gcgaacttttt gctgagttga   1680 aggatcagat cacgcatctt cccgacaacg cagaccgttc cgtggcaaag caaaagttca    1740
aaatcagtaa ccgtcagtgc cgataagttc aaagttaaac ctggtgttga taccaacatt    1800
gaaacgctga tcgaaaacgc gctgaaaaac gctgctgaat gtgcgagctt cttccgcttc    1860
ctcgctcact gactcgctgc gctcggtcgt tcggctgcgg cgagcggtat cagctcactc    1920
aaaggcggta atacggttat ccacagaatc aggggataac gcaggaaaga acatgtgagc    1980
aaaaggccag caaaaggcca ggaaccgtaa aaaggccgcg ttgctggcgt ttttccatag    2040
gctccgcccc cctgacgagc atcacaaaaa tcgacgctca agtcagaggt ggcgaaaccc    2100
gacaggacta taaagatacc aggcgtttcc ccctggaagc tccctcgtgc gctctcctgt    2160
tccgaccctg ccgcttaccg gatacctgtc cgcctttctc ccttcgggaa gcgtggcgct    2220
ttctcaatgc tcacgctgta ggtatctcag ttcggtgtag gtcgttcgct ccaagctggg    2280
ctgtgtgcac gaaccccccg ttcagcccga ccgctgcgcc ttatccggta actatcgtct    2340
tgagtccaac ccggtaagac acgacttatc gccactggca gcagccactg gtaacaggat    2400
tagcagagcg aggtatgtag gcggtgctac agagttcttg aagtggtggc ctaactacgg    2460
ctacactaga aggacagtat ttggtatctg cgctctgctg aagccagtta ccttcggaaa    2520
aagagttggt agctcttgat ccggcaaaca aaccaccgct ggtagcggtg gtttttttgt    2580
ttgcaagcag cagattacgc gcagaaaaaa aggatctcaa gaagatcctt tgatcttttc    2640 tacgggtct gacgctcagt ggaacgatcc gtcga                                2675

<210> SEQ ID NO 15
<211> LENGTH: 23
<212> TYPE: DNA
<213> ORGANISM: Artificial sequence
<220> FEATURE:
<223> OTHER INFORMATION: PCR primer

<400> SEQUENCE: 15
gcgaaagatc tagcatggtc gtc                                              23

<210> SEQ ID NO 16
<211> LENGTH: 24
<212> TYPE: DNA
<213> ORGANISM: Artificial sequence
<220> FEATURE:
<223> OTHER INFORMATION: PCR primer

<400> SEQUENCE: 16
gtgagcagat ctggaaccgt tatc                                             24

<210> SEQ ID NO 17
<211> LENGTH: 23
<212> TYPE: DNA
<213> ORGANISM: Artificial sequence
<220> FEATURE:
<223> OTHER INFORMATION: PCR primer

<400> SEQUENCE: 17
gctggagatc taggtttccc gac                                              23
```

<210> SEQ ID NO 18
<211> LENGTH: 23
<212> TYPE: DNA
<213> ORGANISM: Artificial sequence
<220> FEATURE:
<223> OTHER INFORMATION: PCR primer

<400> SEQUENCE: 18
gggaaagatc tcgtgccagc tgc                                           23

<210> SEQ ID NO 19
<211> LENGTH: 551
<212> TYPE: DNA
<213> ORGANISM: Corynebacterium glutamicum

<400> SEQUENCE: 19
ccgaagatct gaagattcct gatacaaatt ctgttgtgac ggaagatttg ttggaagaaa    60
tctagtcgct cgtctcataa aaacgaccga gcctattggg attaccattg aagccagtgt   120
gagttgcatc acactggctt caaatctgag actttacttt gtggattcac ggggtgtag    180 tgcaattcat aattagcccc attcggggga gcagatcgcg gcgcgaacga tttcaggttc   240
gttccctgca aaactatttt agcgcaagtg ttggaaatgc ccccgtctgg ggtcaatgtc   300
tatttttgaa tgtgtttgta tgattttgaa tccgctgcaa aatctttgtt tccccgctaa   360
agttggggac aggttgacac ggagttgact cgacgaatta tccaatgtga gtaggtttgg   420
tgcgtgagtt ggaaaatttc gccatactcg cccttgggtt ctgtcagctc aagaattctt   480
gagtgaccga tgctctgatt gacctaactg cttgacacat tgcatttcct acaatcttta   540
gaggagacac a                                                       551

<210> SEQ ID NO 20
<211> LENGTH: 425
<212> TYPE: DNA
<213> ORGANISM: Artificial sequence
<220> FEATURE:
<223> OTHER INFORMATION: rrnBT1T2 terminator

<400> SEQUENCE: 20
ctgttttggc ggatgagaga agattttcag cctgatacag attaaatcag aacgcagaag    60
cggtctgata aaacagaatt tgcctggcgg cagtagcgcg gtggtcccac ctgaccccat   120
gccgaactca gaagtgaaac gccgtagcgc cgatggtagt gtggggtctc cccatgcgag   180
agtagggaac tgccaggcat caaataaaac gaaaggctca gtcgaaagac tgggcctttc   240
gttttatctg ttgtttgtcg gtgaacgctc tcctgagtag acaaatccg ccgggagcgg   300 atttgaacgt tgcgaagcaa cggcccggag ggtggcgggc aggacgcccg ccataaactg   360
ccaggcatca aattaagcag aaggccatcc tgacggatgg cctttttgcg tttctacaaa   420
ctctt                                                               425

<210> SEQ ID NO 21
<211> LENGTH: 31
<212> TYPE: DNA
<213> ORGANISM: Artificial sequence
<220> FEATURE:
<223> OTHER INFORMATION: PCR primer

<400> SEQUENCE: 21
ctctgtcgac ccgaagatct gaagattcct g                                  31

<210> SEQ ID NO 22
<211> LENGTH: 46
<212> TYPE: DNA
<213> ORGANISM: Artificial sequence
<220> FEATURE:
<223> OTHER INFORMATION: PCR primer

<400> SEQUENCE: 22
ctctgtcgac ggatccccat ggtgtgtctc tctaaagat tgtagg          46

<210> SEQ ID NO 23
<211> LENGTH: 36
<212> TYPE: DNA
<213> ORGANISM: Artificial sequence
<220> FEATURE:
<223> OTHER INFORMATION: PCR primer

<400> SEQUENCE: 23
ctctgcatgc ccatggctgt tttggcggat gagaga                    36

<210> SEQ ID NO 24
<211> LENGTH: 41
<212> TYPE: DNA
<213> ORGANISM: Artificial sequence
<220> FEATURE:
<223> OTHER INFORMATION: PCR primer

<400> SEQUENCE: 24
ctctgcatgc tcatgaaaga gtttgtagaa acgcaaaaag g              41

<210> SEQ ID NO 25
<211> LENGTH: 2392
<212> TYPE: DNA
<213> ORGANISM: Corynebacterium glutamicum

<400> SEQUENCE: 25
gtgaatgtgg cagcttctca acagcccact cccgccacgg ttgcaagccg tggtcgatcc      60
gccgcccctg agcggatgac aggtgcacag gcaattgttc gatcgctcga ggagcttaac    120
gccgacatcg tgttcggtat tcctggtggt gcggtgctac cggtgtatga cccgctctat    180
tcctccacaa aggtgcgcca cgtcttggtg cgccacgagc agggcgcagg ccacgcagca    240
accggctacg cgcaggttac tggacgcgtt ggcgtctgca ttgcaacctc tggcccagga    300
gcaaccaact tggttacccc aatcgctgat gcaaacttgg actccgttcc catggttgcc    360
atcaccggcc aggtcggaag tggcctgctg ggtaccgacg cttt ccagga agccgatatc    420
cgcggcatca ccatgccagt gaccaagcac aacttcatgg tcaccgaccc caacgacatt    480
ccacaggcat ggctgaggc attccacctc gcgattactg gtcgccctgg ccctgttctg    540
gtggatattc ctaaggatgt ccagaacgct gaattggatt tcgtctggcc accaaagatc    600
gacctgccag gctaccgccc agtttcaaca ccacatgctc gccagatcga gcaggcagtc    660
aagctgatcg gtgaggccaa gaagcccgtc ctttacgttg gaggcggcgt tatcaaggct    720
gacgcacacg aagagcttcg tgcgttcgct gagtacaccg gcatcccagt tgtcaccacc    780
ttgatggctt gggtacttt cccagagtct cacgagctgc acatgggtat gccaggcatg    840
catggcactg tgtccgctgt tggtgcactg cagcgcagcg acctgctgat tgctatcggc    900
tcccgctttg atgaccgcgt caccggtgac gttgacacct tcgcgcctga cgccaagatc    960
attcacgccg atattgatcc tgccgaaatc ggaaagatca agcaggttga ggttccaatc   1020
gtgggcgatg cccgcgaagt tcttgctcgt ctgctggaaa ccaccaaggc aagcaaggca   1080

```
gagaccgagg acatctccga gtgggttgac tacctcaagg gcctcaaggc acgtttccca   1140
cgtggctacg acgagcagcc aggcgatctg ctggcaccac agtttgtcat tgaaaccctg   1200
tccaaggaag ttggccccga cgcaatttac tgcgccggcg tcggacagca ccaaatgtgg   1260
gcagctcagt tcgttgactt tgaaaagcca cgcacctggc tcaactccgg tggactgggc   1320
accatgggct acgcagttcc tgcggcccett ggagcaaagg ctggcgcacc tgacaaggaa   1380
gtctgggcta tcgacggcga cggctgtttc cagatgacca accaggaact caccaccgcc   1440
gcagttgaag gtttccccat taagatcgca ctaatcaaca acggaaacct gggcatggtt   1500
cgccaatggc agaccctatt ctatgaagga cggtactcaa atactaaact tcgtaaccag   1560
ggcgagtaca tgcccgactt tgttgccctt tctgagggac ttggctgtgt tgccatccgc   1620
gtcaccaaag cggaggaagt actgccagcc atccaaaagg ctcgagaaat caacgaccgc   1680
ccagtagtca tcgacttcat cgtcggtgaa gacgcacagg tatggccaat ggtgtctgct   1740
ggatcatcca actccgatat ccagtacgca ctcggattgc gcccattctt tgacggcgac   1800
gaatcagctg cagaagaccc tgcagacatt catgcttccg ttgattcgac cgaggcataa   1860
ggagagaccc aagatggcta attctgacgt caccccgccac atcctgtccg tactcgttca   1920
ggacgtagac ggaatcattt cccgcgtatc aggtatgttc acccgacgcg cattcaacct   1980
cgtgtccctc gtgtctgcaa agaccgaaac acacggcatc aaccgcatca cggttgttgt   2040
cgacgccgac gagctcaaca ttgagcagat caccaagcag ctcaacaagc tgatcccggt   2100
gctcaaagtc gtgcgacttg atgaagagac cactatcgcc cgcgcaatca tgctggttaa   2160
ggtctctgcg acagcacca accgtccgca gatcgtcgac gccgcgaaca tcttccgcgc   2220
ccgagtcgtc gacgtggctc cagactctgt ggttattgaa tccacaggca ccccaggcaa   2280
gctccgcgct ctgcttgatg tgatggaacc attcggaatc cgcgaactga tccaatccgg   2340
acagattgca ctcaaccgcg gtccgaagac catggctccg gccaagatct aa             2392
```

<210> SEQ ID NO 26
<211> LENGTH: 1017
<212> TYPE: DNA
<213> ORGANISM: Corynebacterium glutamicum

<400> SEQUENCE: 26

```
atggctattg aactgcttta tgatgctgac gctgacctct ccttgatcca gggccgtaag     60
gttgccatcg ttggctacgg ctcccagggc cacgcacact cccagaacct ccgcgattct    120
ggcgttgagg ttgtcattgg tctgcgcgag ggctccaagt ccgcagagaa ggcaaaggaa    180
gcaggcttcg aagtcaagac caccgctgag gctgcagctt gggctgacgt catcatgctc    240
ctggctccag acacctccca ggcagaaatc ttcaccaacg catcgagcc aaacctgaac    300 gcaggcgacg cactgctgtt cggccacggc ctgaacattc acttcgacct gatcaagcca    360
gctgacgaca tcatcgttgg catggttgcg ccaaagggcc caggccactt ggttcgccgt    420
cagttcgttg atggcaaggg tgttccttgc ctcatcgcag tcgaccagga cccaaccgga    480
accgcacagg ctctgacccect gtcctacgca gcagcaatcg tggcgcacg cgcaggcgtt    540 atcccaacca ccttcgaagc tgagaccgtc accgacctct cggcgagca ggctgttctc    600 tgcggtggca ccgaggaact ggtcaaggtt ggcttcgagg ttctcaccga agctggctac    660
gagccagaga tggcatactt cgaggttctt cacgagctca agctcatcgt tgacctcatg    720
ttcgaaggtg gcatcagcaa catgaactac tctgtttctg acaccgctga gttcggtggc    780
```

| | |
|---|---|
| tacctctccg gcccacgcgt catcgatgca gacaccaagt cccgcatgaa ggacatcctg | 840 |
| accgatatcc aggacggcac cttcaccaag cgcctcatcg caaacgttga gaacggcaac | 900 |
| accgagcttg agggtcttcg tgcttcctac aacaaccacc caatcgagga gaccggcgct | 960 |
| aagctccgcg acctcatgag ctgggtcaag gttgacgctc gcgcagaaac cgcttaa | 1017 |

<210> SEQ ID NO 27
<211> LENGTH: 1964
<212> TYPE: DNA
<213> ORGANISM: Corynebacterium glutamicum

<400> SEQUENCE: 27

| | |
|---|---|
| gagcagattt gaaaagcgca tcatgatccc acttcgttca aaagtcacca ccgtcggtcg | 60 |
| caatgcagct ggcgctcgcg ccctttggcg tgccaccggc accaaggaaa atgagttcgg | 120 |
| caagccaatt gttgccatcg tgaactccta cacccagttc gtgcccggac acgttcacct | 180 |
| taagaacgtc ggcgatattg tggcagatgc agtgcgcaaa gccggtggcg ttccaaaaga | 240 |
| attcaacacc atcgccgtcg atgacggcat cgccatggga cacggcggca tgctgtactc | 300 |
| cctgccatcc cgtgaaatca tcgccgactc cgtcgaatac atggtcaacg cacacaccgc | 360 |
| cgacgccatg gtgtgtatct ccaactgtga caagatcacc ccaggcatgc tcaacgcagc | 420 |
| aatgcgcctg aacatcccag tggtcttcgt ttccggtggc ccaatggaag ctggcaaggc | 480 |
| tgtcgtcgtt gacggcgttg cacacgcacc aaccgacctc atcaccgcga tctccgcatc | 540 |
| cgcaagcgat gcagtcgacg acgcaggcct tgcagccgtt gaagcatccg catgcccaac | 600 |
| ctgtggctcc tgctccggta tgttcaccgc gaactccatg aactgcctca ccgaagctct | 660 |
| gggactttct ctcccaggca acggctccac cctggcaacc cacgcagcac gtcgcgcact | 720 |
| gtttgaaaag gccggcgaaa ccgtcgttga actgtgccgc cgctactacg gtgaagaaga | 780 |
| cgaatccgtt ctgccacgtg gcattgccac caagaaggca ttcgaaaacg caatggcact | 840 |
| ggatatggcc atgggtggat ccaccaacac catcctccac atcctcgcag ctgcccagga | 900 |
| aggcgaagtt gacttcgacc tcgcagacat cgacgaactg tccaaaaacg tcccctgcct | 960 |
| gtccaaggtt gcaccaaact ccgactacca catggaagac gtccaccgcg ccggtggcat | 1020 |
| tccagcactg ctcggcgagc tcaaccgcgg tggcctgctg aataaggacg tccactccgt | 1080 |
| tcactccaac gaccttgaag gttggttgga tgactgggat atccgctctg caagaccac | 1140 |
| cgaagtagca accgaactct ccacgcagc cccaggtggc atccgcacca ccgaagcatt | 1200 |
| ctccaccgag aaccgctggg acgaactcga caccgacgct gccaagggct gcatccgcga | 1260 |
| cgttgaacac gcctacaccg ccgacggcgg cctggttgtt cttcgcggca acatctcccc | 1320 |
| tgacggcgca gtgatcaagt ccgcaggtat cgaagaagag ctgtggaact tcaccggacc | 1380 |
| agcacgagtt gtcgaaagcc aggaagaggc agtctctgtc atcctgacca agaccatcca | 1440 |
| agctggcgaa gttctggtcg tccgctacga aggcccatca ggtggaccag gcatgcagga | 1500 |
| aatgcttcac ccaaccgcat tcctcaaggg atccggcctg gcaagaagt gtgcactgat | 1560 |
| caccgacggc cgtttctccg gaggttcctc aggactgtcc atcggccacg tctccccaga | 1620 |
| agcagcacac ggcggagtca ttggtctgat cgaaaacggc gacatcgttt ccatcgacgt | 1680 |
| tcacaaccgc aagctcgaag ttcaggtctc caacgaggaa ctccagcgcc gccgcgacgc | 1740 |
| tatgaacgcc tccagaaagc catggcagcc agtcaaccgt aaccgcgttg tcaccaaggc | 1800 |
| actgcgcgca tacgcaaaga tggctaccte cgctgataag ggtgcagtcc gtcaggtcga | 1860 |
| ctaacccttt gtaagtgttt gagcaccggt tccctacttt gggttccggt gcttttcat | 1920 |

```
gtcttgggct gtgtgggcgt ggtggagctc cccgttgcaa atac            1964
```

<210> SEQ ID NO 28
<211> LENGTH: 1264
<212> TYPE: DNA
<213> ORGANISM: Corynebacterium glutamicum

<400> SEQUENCE: 28

```
catcccataa aatggggctg actagtgtat ctgtcaggta gcaggtgtac cttgaaatcc   60
atgacgtcat tagagttcac agtaacccgt accgaaaatc cgacgtcacc cgatcgtctg  120
aaggaaattc ttgccgcacc gaagttcggt aagttcttca ccgaccacat ggtgaccatt  180
gactggaacg agttggaagg ctggcacaac gcccaattag tgccatacgc gccgattcct  240
atggatcctg ccaccaccgt attccactac ggacaggcaa ttttgaggg aattaaggcc   300
taccgccatt cggacgaaac catcaagact ttccgtcctg atgaaaacgc cgaacgtatg  360
cagcgttcag cagctcgaat ggcaatgcca cagttgccaa ccgaggactt tattaaagca  420
cttgaactgc tggtagacgc agatcaggat tgggttcctg agtacggcgg ggaagcttcc  480
ctctacctgc gcccattcat gatctccacc gaaattggct gggtgtcag cccagctgat   540
gcctataagt tcctggtcat cgcatcccca gtcggcgctt acttcaccgg tggaatcaag  600
cctgtttccg tctggctgag cgaagattac gtccgtgctg cacccggcgg aactggtgac  660
gccaaatttg ctggcaacta cgcggcttct ttgcttgccc agtcccaggc tgcggaaaag  720
ggctgtgacc aggtcgtatg gttggatgcc atcgagcata agtacatcga gaaatgggt   780
ggcatgaacc ttgggttcat ctaccgcaac ggcgaccacg tcaagctagt caccccctgaa  840
ctttccggct cactacttcc aggcatcacc cgcaagtcac ttctacaagt agcacgcgac  900
ttgggctacg aagtagaaga gcgaaagatc accaccaccg agtgggaaga agacgcaaag  960
tctggcgcca tgaccgaggc atttgcttgc ggtactgcag ctgttatcac ccctgttggc 1020
accgtaaaat cagctcacgg caccttcgaa gtgaacaaca atgaagtcgg agaaatcacg 1080
atgaagcttc gtgaaaccct caccggaatt cagcaaggaa acgttgaaga ccaaaacgga 1140
tggctttacc cactggttgg ctaaatcaac cggttttaag accccgctgc attaaaccct 1200
gatttattgc agcggggttt ttgcgttgac cagctcttat gagacgtagg gggtggagtc 1260
aggg                                                            1264
```

<210> SEQ ID NO 29
<211> LENGTH: 28
<212> TYPE: DNA
<213> ORGANISM: Artificial sequence
<220> FEATURE:
<223> OTHER INFORMATION: PCR primer

<400> SEQUENCE: 29

```
ctcttcatga atgtggcagc ttctcaac                                    28
```

<210> SEQ ID NO 30
<211> LENGTH: 28
<212> TYPE: DNA
<213> ORGANISM: Artificial sequence
<220> FEATURE:
<223> OTHER INFORMATION: PCR primer

<400> SEQUENCE: 30

```
ctcttcatga ttagatcttg gccggagc                                    28
```

<210> SEQ ID NO 31
<211> LENGTH: 31
<212> TYPE: DNA
<213> ORGANISM: Artificial sequence
<220> FEATURE:
<223> OTHER INFORMATION: PCR primer

<400> SEQUENCE: 31
ctctccatgg ctattgaact gctttatgat g         31

<210> SEQ ID NO 32
<211> LENGTH: 35
<212> TYPE: DNA
<213> ORGANISM: Artificial sequence
<220> FEATURE:
<223> OTHER INFORMATION: PCR primer

<400> SEQUENCE: 32
ctctccatgg agatctttaa gcggtttctg cgcga     35

<210> SEQ ID NO 33
<211> LENGTH: 33
<212> TYPE: DNA
<213> ORGANISM: Artificial sequence
<220> FEATURE:
<223> OTHER INFORMATION: PCR primer

<400> SEQUENCE: 33
gacccgggga gcagatttga aaagcgcatc atg       33

<210> SEQ ID NO 34
<211> LENGTH: 39
<212> TYPE: DNA
<213> ORGANISM: Artificial sequence
<220> FEATURE:
<223> OTHER INFORMATION: PCR primer

<400> SEQUENCE: 34
gacccggggg taccgtattt gcaacgggga gctccacca  39

<210> SEQ ID NO 35
<211> LENGTH: 33
<212> TYPE: DNA
<213> ORGANISM: Artificial sequence
<220> FEATURE:
<223> OTHER INFORMATION: PCR primer

<400> SEQUENCE: 35
gacccgggca tcccataaaa tggggctgac tag       33

<210> SEQ ID NO 36
<211> LENGTH: 39
<212> TYPE: DNA
<213> ORGANISM: Artificial sequence
<220> FEATURE:
<223> OTHER INFORMATION: PCR primer

<400> SEQUENCE: 36
gacccgggga gctcccctga ctccaccccc tacgtctca  39

<210> SEQ ID NO 37
<211> LENGTH: 2392
<212> TYPE: DNA
<213> ORGANISM: Artificial sequence
<220> FEATURE:
<223> OTHER INFORMATION: ilvBN gene mutant

```
<400> SEQUENCE: 37
gtgaatgtgg cagcttctca acagcccact cccgccacgg ttgcaagccg tggtcgatcc    60
gccgcccctg agcggatgac aggtgcacag gcaattgttc gatcgctcga ggagcttaac   120
gccgacatcg tgttcggtat tcctggtggt gcggtgctac cggtgtatga cccgctctat   180
tcctccacaa aggtgcgcca cgtcttggtg cgccacgagc agggcgcagg ccacgcagca   240
accggctacg cgcaggttac tggacgcgtt ggcgtctgca ttgcaacctc tggcccagga   300
gcaaccaact tggttacccc aatcgctgat gcaaacttgg actccgttcc catggttgcc   360
atcaccggcc aggtcggaag tggcctgctg ggtaccgacg ctttccagga agccgatatc   420
cgcggcatca ccatgccagt gaccaagcac aacttcatgg tcaccgaccc caacgacatt   480
ccacaggcat tggctgaggc attccacctc gcgattactg gtcgccctgg ccctgttctg   540
gtggatattc ctaaggatgt ccagaacgct gaattggatt tcgtctggcc accaaagatc   600
gacctgccag gctaccgccc agtttcaaca ccacatgctc gccagatcga gcaggcagtc   660
aagctgatcg gtgaggccaa gagcccgtc ctttacgttg gaggcggcgt tatcaaggct   720
gacgcacacg aagagcttcg tgcgttcgct gagtacaccg gcatcccagt tgtcaccacc   780
ttgatggctt tgggtacttt cccagagtct cacgagctgc acatgggtat gccaggcatg   840
catggcactg tgtccgctgt tggtgcactg cagcgcagcg acctgctgat tgctatcggc   900
tcccgctttg atgaccgcgt caccggtgac gttgacacct cgcgcctga cgccaagatc   960
attcacgccg atattgatcc tgccgaaatc ggaaagatca agcaggttga ggttccaatc  1020
gtgggcgatg cccgcgaagt tcttgctcgt ctgctggaaa ccaccaaggc aagcaaggca  1080
gagaccgagg acatctccga gtgggttgac tacctcaagg gcctcaaggc acgtttccca  1140
cgtggctacg acgagcagcc aggcgatctg ctggcaccac agtttgtcat tgaaaccctg  1200
tccaaggaag ttggcccccga cgcaatttac tgcgccggcg tcggacagca ccaaatgtgg  1260
gcagctcagt tcgttgactt tgaaaagcca cgcacctggc tcaactccgg tggactgggc  1320
accatgggct acgcagttcc tgcggcccct ggagcaaagg ctggcgcacc tgacaaggaa  1380
gtctgggcta tcgacggcga cggctgtttc cagatgacca accaggaact caccaccgcc  1440
gcagttgaag gttttcccat taagatcgca ctaatcaaca acggaaacct gggcatggtt  1500
cgccaatggc agaccctatt ctatgaagga cggtactcaa atactaaact tcgtaaccag  1560
ggcgagtaca tgcccgactt tgttgccctt tctgagggac ttggctgtgt gccatccgc  1620
gtcaccaaag cggaggaagt actgccagcc atccaaaagg ctcgagaaat caacgaccgc  1680
ccagtagtca tcgacttcat cgtcggtgaa gacgcacagg tatggccaat ggtgtctgct  1740
ggatcatcca actccgatat ccagtacgca ctcggattgc gcccattctt tgacggcgac  1800
gaatcagctg cagaagaccc tgcagacatt catgcttccg ttgattcgac cgaggcataa  1860
ggagagaccc aagatggcta attctgacgt caccccgccac atcctgtccg tactcgttca  1920
ggacgtagac ggaatcattt cccgcgtatc aggtatgttc acccgacgcg cattcaacct  1980
cgtgtccctc gtgtctgcaa agaccgaaac acacggcatc aaccgcatca cggttgttgt  2040
cgacgccgac gagctcaaca ttgagcagat caccaagcag ctcaacaagc tgatcccggt  2100
gctcaaagtc gtgcgacttg atgaagagac cactatcgcc cgcgcaatca tgctggttaa  2160
ggtctctgcg gacagcacca accgtccgca gatcgtcgac gccgcaaca tcttccgcgc  2220
ccgagtcgtc gacgtggctc cagactctgt ggttattgaa tccacaggca ccccaggcaa  2280
```

-continued

```
gctccgcgct ctgcttgatg tgatggaacc attcggaatc cgcgaactga tccaatccga   2340
acagattgca ctcaaccgcg gtccgaagac catggctccg gccaagatct aa           2392

<210> SEQ ID NO 38
<211> LENGTH: 28
<212> TYPE: DNA
<213> ORGANISM: Artificial sequence
<220> FEATURE:
<223> OTHER INFORMATION: PCR primer

<400> SEQUENCE: 38
ctcttcatga atgtggcagc ttctcaac                                        28

<210> SEQ ID NO 39
<211> LENGTH: 28
<212> TYPE: DNA
<213> ORGANISM: Artificial sequence
<220> FEATURE:
<223> OTHER INFORMATION: PCR primer

<400> SEQUENCE: 39
ctcttcatga ttagatcttg gccggagc                                        28

<210> SEQ ID NO 40
<211> LENGTH: 1095
<212> TYPE: DNA
<213> ORGANISM: Lisinibacillus sphaericus

<400> SEQUENCE: 40
atggaaatct tcaagtatat ggaaaagtat gattatgaac aattggtatt ttgccaagac     60
gaagcatctg ggttaaaagc gattatcgct atccatgaca caacacttgg accagcatta    120
ggtggtgctc gtatgtggac ctacgcgaca gaagaaaatg cgattgagga tgcattaaga    180
ttagcacgcg ggatgacata taaaaatgca gctgctggtt taaaccttgg cggtggaaaa    240
acggtcatta ttggggaccc atttaaagat aaaaacgaag aaatgttccg tgctttaggt    300
cgtttcattc aaggattaaa cggtcgctat attaccgctg aagatgttgg tacaaccgta    360
acagatatgg atttaatcca tgaggaaaca aattacgtta caggtatatc gccagcgttt    420
ggttcatcgg gtaatccttc accagtaact gcttatggcg tttatcgtgg catgaaagca    480
gcggcgaaag aagcatttgg tacggatatg ctagaaggtc gtactatatc ggtacaaggg    540
ctaggaaacg tagcttacaa gctttgcgag tatttacata atgaaggtgc aaaacttgta    600
gtaacagata ttaaccaagc ggctattgat cgtgttgtca atgattttgg cgctacagca    660
gttgcacctg atgaaatcta ttcacaagaa gtcgatattt tctcaccgtg tgcacttggc    720
gcaattttaa atgacgaaac gattccgcaa ttaaaagcaa aagttattgc tggttctgct    780
aataaccaac tacaagattc acgacatgga gattatttac acgagctagg cattgtttat    840
gcacctgact atgtcattaa tgcaggtggt gtaataaatg tcgcggacga attatatggc    900
tataatcgtg aacgagcgtt gaaacgtgta gatggtattt acgatagtat tgaaaaaatc    960
tttgaaattt ccaaacgtga tagtattcca acatatgttg cggcaaatcg tttggcagaa   1020
gaacgtattg ctcgtgtagc gaaatcgcgt agtcagttct taaaaaatga aaaaaatatt   1080
ttgaacggcc gttaa                                                    1095

<210> SEQ ID NO 41
<211> LENGTH: 40
<212> TYPE: DNA
<213> ORGANISM: Artificial sequence
```

```
<220> FEATURE:
<223> OTHER INFORMATION: PCR primer

<400> SEQUENCE: 41
acgcccggga ggaggtacgg atggaaatct tcaagtatat                          40

<210> SEQ ID NO 42
<211> LENGTH: 40
<212> TYPE: DNA
<213> ORGANISM: Artificial sequence
<220> FEATURE:
<223> OTHER INFORMATION: PCR primer

<400> SEQUENCE: 42
tcggcccggg gagctcttaa cggccgttca aaatattttt                          40

<210> SEQ ID NO 43
<211> LENGTH: 2160
<212> TYPE: DNA
<213> ORGANISM: Corynebacterium glutamicum

<400> SEQUENCE: 43
gctgtgcagg tcgtaaatca ctgcataatt cgtgtcgctc aaggcgcact cccgttctgg    60
ataatgtttt ttgcgccgac atcataacgg ttctggcaaa tattctgaaa tgagctgttg   120
acaattaatc atcggctcgt ataatgtgtg gaattgtgag cggataacaa tttcacacag   180
gaaacagaat tcccggggag cagatttgaa aagcgcatca tgatcccact tcgttcaaaa   240
gtcaccaccg tcgtcgcaa tgcagctggc gctcgcgccc tttggcgtgc caccggcacc   300
aaggaaaatg agttcggcaa gccaattgtt gccatcgtga actcctacac ccagttcgtg   360
cccggacacg ttcaccttaa gacgtcggc gatattgtgg cagatgcagt gcgcaaagcc   420
ggtggcgttc caaaagaatt caacaccatc gccgtcgatg acggcatcgc catgggacac   480
ggcggcatgc tgtactccct gccatcccgt gaaatcatcg ccgactccgt cgaatacatg   540
gtcaacgcac acaccgccga cgccatggtg tgtatctcca actgtgacaa gatcaccccca   600
ggcatgctca acgcagcaat gcgcctgaac atcccagtgg tcttcgtttc cggtggccca   660
atggaagctg gcaaggctgt cgtcgttgac ggcgttgcac acgcaccaac cgacctcatc   720
accgcgatct ccgcatccgc aagcgatgca gtcgacgacg caggccttgc agccgttgaa   780
gcatccgcat gcccaacctg tggctcctgc tccggtatgt tcaccgcgaa ctccatgaac   840
tgcctcaccg aagctctggg actttctctc ccaggcaacg gctccaccct ggcaacccac   900
gcagcacgtc gcgcactgtt tgaaaaggcc ggcgaaaccg tcgttgaact gtgccgccgc   960
tactacggtg aagaagacga atccgttctg ccacgtggca ttgccaccaa gaaggcattc  1020
gaaaacgcaa tggcactgga tatggccatg ggtggatcca ccaacaccat cctccacatc  1080
ctcgcagctg cccaggaagg cgaagttgac ttcgacctcg cagacatcga cgaactgtcc  1140
aaaaacgtcc cctgcctgtc caaggttgca ccaaactccg actaccacat ggaagacgtc  1200
caccgcgccg gtggcattcc agcactgctc ggcgagctca accgcggtgg cctgctgaat  1260
aaggacgtcc actccgttca ctccaacgac cttgaaggtt ggttggatga ctgggatatc  1320
cgctctggca agaccaccga agtagcaacc gaactcttcc acgcagcccc aggtggcatc  1380
cgcaccaccg aagcattctc caccgagaac cgctgggacg aactcgacac cgacgctgcc  1440
aagggctgca tccgcgacgt tgaacacgcc tacaccgccg acggcggcct ggttgttctt  1500
cgcggcaaca tctcccctga cggcgcagtg atcaagtccg caggtatcga agaagagctg  1560
```

```
tggaacttca ccggaccagc acgagttgtc gaaagccagg aagaggcagt ctctgtcatc    1620
ctgaccaaga ccatccaagc tggcgaagtt ctggtcgtcc gctacgaagg cccatcaggt    1680
ggaccaggca tgcaggaaat gcttcaccca accgcattcc tcaagggatc cggcctgggc    1740
aagaagtgtg cactgatcac cgacggccgt ttctccggag gttcctcagg actgtccatc    1800
ggccacgtct ccccagaagc agcacacggc ggagtcattg gtctgatcga aaacggcgac    1860
atcgtttcca tcgacgttca caaccgcaag ctcgaagttc aggtctccaa cgaggaactc    1920
cagcgccgcc gcgacgctat gaacgcctcc gagaagccat ggcagccagt caaccgtaac    1980
cgcgttgtca ccaaggcact gcgcgcatac gcaaagatgg ctacctccgc tgataagggt    2040
gcagtccgtc aggtcgacta acccttttgta agtgtttgag caccggttcc ctactttggg   2100
ttccggtgct ttttcatgtc ttgggctgtg tgggcgtggt ggagctcccc gttgcaaata    2160
```

```
<210> SEQ ID NO 44
<211> LENGTH: 39
<212> TYPE: DNA
<213> ORGANISM: Artificial sequence
<220> FEATURE:
<223> OTHER INFORMATION: PCR primer

<400> SEQUENCE: 44
atatcctgca ggctagcgct gtgcaggtcg taaatcact                             39

<210> SEQ ID NO 45
<211> LENGTH: 38
<212> TYPE: DNA
<213> ORGANISM: Artificial sequence
<220> FEATURE:
<223> OTHER INFORMATION: PCR primer

<400> SEQUENCE: 45
atatgctagc tcctgcaggt atttgcaacg gggagctc                              38

<210> SEQ ID NO 46
<211> LENGTH: 1462
<212> TYPE: DNA
<213> ORGANISM: Corynebacterium glutamicum

<400> SEQUENCE: 46
ctgtgcaggt cgtaaatcac tgcataattc gtgtcgctca aggcgcactc ccgttctgga      60
taatgttttt tgcgccgaca tcataacggt tctggcaaat attctgaaat gagctgttga    120
caattaatca tcggctcgta taatgtgtgg aattgtgagc ggataacaat ttcacacagg    180
aaacagaatt cccgggcatc ccataaaatg gggctgacta gtgtatctgt caggtagcag    240
gtgtaccttg aaatccatga cgtcattaga gttcacagta cccgtaccg aaaatccgac     300 gtcacccgat cgtctgaagg aaattcttgc cgcaccgaag ttcggtaagt tcttcaccga    360
ccacatggtg accattgact ggaacgagtt ggaaggctgg cacaacgccc aattagtgcc    420
atacgcgccg attcctatgg atcctgccac caccgtattc cactacggac aggcaatttt    480
tgagggaatt aaggcctacc gccattcgga cgaaaccatc aagactttcc gtcctgatga    540
aaacgccgaa cgtatgcagc gttcagcagc tcgaatggca atgccacagt tgccaaccga    600
ggactttatt aaagcacttg aactgctggt agacgcagat caggattggg ttcctgagta    660
cggcggggaa gcttccctct acctgcgccc attcatgatc tccaccgaaa ttggcttggg    720
tgtcagccca gctgatgcct ataagttcct ggtcatcgca tccccagtcg gcgcttactt    780
caccggtgga atcaagcctg tttccgtctg gctgagcgaa gattacgtcc gtgctgcacc    840
```

-continued

```
cggcggaact ggtgacgcca aatttgctgg caactacgcg gcttctttgc ttgcccagtc      900
ccaggctgcg gaaaagggct gtgaccaggt cgtatggttg gatgccatcg agcataagta      960
catcgaagaa atgggtggca tgaaccttgg gttcatctac cgcaacggcg accacgtcaa     1020
gctagtcacc cctgaacttt ccggctcact acttccaggc atcacccgca agtcacttct     1080
acaagtagca cgcgacttgg gctacgaagt agaagagcga agatcacca ccaccgagtg      1140 ggaagaagac gcaaagtctg gcgccatgac cgaggcattt gcttgcggta ctgcagctgt     1200
tatcacccct gttggcaccg taaaatcagc tcacggcacc ttcgaagtga acaacaatga     1260
agtcggagaa atcacgatga agcttcgtga accctcacc ggaattcagc aaggaaacgt      1320
tgaagaccaa aacggatggc tttacccact ggttggctaa atcaaccggt tttaagaccc     1380
cgctgcatta aaccctgatt tattgcagcg gggttttgc gttgaccagc tcttatgaga      1440 cgtaggggt ggagtcaggg at                                               1462
```

<210> SEQ ID NO 47
<211> LENGTH: 1303
<212> TYPE: DNA
<213> ORGANISM: Lisinibacillus sphaericus

<400> SEQUENCE: 47

```
ctgtgcaggt cgtaaatcac tgcataattc gtgtcgctca aggcgcactc ccgttctgga      60
taatgttttt tgcgccgaca tcataacggt tctggcaaat attctgaaat gagctgttga     120
caattaatca tcggctcgta taatgtgtgg aattgtgagc ggataacaat ttcacacagg     180
aaacagaatt cccgggagga ggtacggatg gaaatcttca gtatatgga aaagtatgat      240 tatgaacaat ggtatttttg ccaagacgaa gcatctgggt taaaagcgat tatcgctatc     300
catgacacaa cacttggacc agcattaggt ggtgctcgta tgtggaccta cgcgacagaa     360
gaaaatgcga ttgaggatgc attaagatta gcacgcggga tgacatataa aaatgcagct     420
gctggtttaa accttggcgg tggaaaaacg gtcattattg gggacccatt taaagataaa     480
aacgaagaaa tgttccgtgc tttaggtcgt ttcattcaag gattaaacgg tcgctatatt     540
accgctgaag atgttggtac aaccgtaaca gatatggatt taatccatga ggaaacaaat     600
tacgttacag gtatatcgcc agcgtttggt tcatcgggta atccttcacc agtaactgct     660
tatggcgttt atcgtggcat gaaagcagcg gcgaaagaag catttggtac ggatatgcta     720
gaaggtcgta ctatatcggt acaagggcta ggaaacgtag cttacaagct tgcgagtat      780 ttacataatg aaggtgcaaa acttgtagta acagatatta accaagcggc tattgatcgt     840
gttgtcaatg attttggcgc tacagcagtt gcacctgatg aaatctattc acaagaagtc     900
gatattttct caccgtgtgc acttggcgca atttaaatg acgaaacgat tccgcaatta     960
aaagcaaaag ttattgctgg ttctgctaat aaccaactac aagattcacg acatggagat    1020
tatttacacg agctaggcat tgtttatgca cctgactatg tcattaatgc aggtggtgta    1080
ataaatgtcg cggacgaatt atatggctat aatcgtgaac gagcgttgaa acgtgtagat    1140
ggtatttacg atagtattga aaaaatcttt gaaatttcca aacgtgatag tattccaaca    1200
tatgttgcgg caaatcgttt ggcagaagaa cgtattgctc gtgtagcgaa atcgcgtagt    1260
cagttcttaa aaaatgaaaa aaatatttg aacggccgtt aac                       1303
```

<210> SEQ ID NO 48
<211> LENGTH: 39
<212> TYPE: DNA

```
<213> ORGANISM: Artificial sequence
<220> FEATURE:
<223> OTHER INFORMATION: PCR primer

<400> SEQUENCE: 48
atatgctagc tcctgcaggc tgtgcaggtc gtaaatcac                                   39

<210> SEQ ID NO 49
<211> LENGTH: 38
<212> TYPE: DNA
<213> ORGANISM: Artificial sequence
<220> FEATURE:
<223> OTHER INFORMATION: PCR primer

<400> SEQUENCE: 49
atatcctgca ggctagcatc cctgactcca cccctac                                    38

<210> SEQ ID NO 50
<211> LENGTH: 39
<212> TYPE: DNA
<213> ORGANISM: Artificial sequence
<220> FEATURE:
<223> OTHER INFORMATION: PCR primer

<400> SEQUENCE: 50
atatgctagc tcctgcaggc tgtgcaggtc gtaaatcac                                   39

<210> SEQ ID NO 51
<211> LENGTH: 38
<212> TYPE: DNA
<213> ORGANISM: Artificial sequence
<220> FEATURE:
<223> OTHER INFORMATION: PCR primer

<400> SEQUENCE: 51
atgccctgca ggctagcgtt aacggccgtt caaaatat                                    38

<210> SEQ ID NO 52
<211> LENGTH: 1017
<212> TYPE: DNA
<213> ORGANISM: Corynebacterium glutamicum

<400> SEQUENCE: 52
atggctattg aactgcttta tgatgctgac gctgacctct ccttgatcca gggccgtaag           60
gttgccatcg ttggctacgg ctcccagggc cacgcacact cccagaacct ccgcgattct          120
ggcgttgagg ttgtcattgg tctgcgcgag ggctccaagt ccgcagagaa ggcaaaggaa          180
gcaggcttcg aagtcaagac caccgctgag gctgcagctt gggctgacgt catcatgctc          240
ctggctccag acacctccca ggcagaaatc ttcaccaacg acatcgagcc aaacctgaac          300
gcaggcgacg cactgctgtt cggccacggc ctgaacattc acttcgacct gatcaagcca          360
gctgacgaca tcatcgttgg catggttgcg ccaaagggcc aggccacttt ggttcgccgt          420
cagttcgttg atggcaaggg tgttccttgc ctcatcgcag tcgaccagga cccaaccgga          480
accgcacagg ctctgaccct gtcctacgca gcagcaatcg gtggcgcacg cgcaggcgtt          540
atcccaacca ccttcgaagc tgagaccgtc accgacctct cggcgagca ggctgttctc          600
tgcggtggca ccgaggaact ggtcaaggtt ggcttcgagg ttctcaccga agctggctac          660
gagccagaga tggcatactt cgaggttctt cacgagctca agctcatcgt tgacctcatg          720
ttcgaaggtg gcatcagcaa catgaactac tctgttctg acaccgctga gttcggtggc          780
tacctctccg gcccacgcgt catcgatgca gacaccaagt cccgcatgaa ggacatcctg          840
```

| | | |
|---|---|---|
| accgatatcc aggacggcac cttcaccaag cgcctcatcg caaacgttga gaacggcaac | 900 | |
| accgagcttg agggtcttcg tgcttcctac aacaaccacc caatcgagga gaccggcgct | 960 | |
| aagctccgcg acctcatgag ctgggtcaag gttgacgctc gcgcagaaac cgcttaa | 1017 | |

<210> SEQ ID NO 53
<211> LENGTH: 17
<212> TYPE: DNA
<213> ORGANISM: Artificial sequence
<220> FEATURE:
<223> OTHER INFORMATION: PCR primer

<400> SEQUENCE: 53
cgcacacggc cagaacc                                                  17

<210> SEQ ID NO 54
<211> LENGTH: 17
<212> TYPE: DNA
<213> ORGANISM: Artificial sequence
<220> FEATURE:
<223> OTHER INFORMATION: PCR primer

<400> SEQUENCE: 54
ggttctggcc gtgtgcg                                                  17

<210> SEQ ID NO 55
<211> LENGTH: 19
<212> TYPE: DNA
<213> ORGANISM: Artificial sequence
<220> FEATURE:
<223> OTHER INFORMATION: PCR primer

<400> SEQUENCE: 55
cattggtgag ttcgagggc                                                19

<210> SEQ ID NO 56
<211> LENGTH: 19
<212> TYPE: DNA
<213> ORGANISM: Artificial sequence
<220> FEATURE:
<223> OTHER INFORMATION: PCR primer

<400> SEQUENCE: 56
gccctcgaac tcaccaatg                                                19

<210> SEQ ID NO 57
<211> LENGTH: 1017
<212> TYPE: DNA
<213> ORGANISM: Artificial sequence
<220> FEATURE:
<223> OTHER INFORMATION: ilvC gene mutant

<400> SEQUENCE: 57

| | | |
|---|---|---|
| atggctattg aactgcttta tgatgctgac gctgacctct ccttgatcca gggccgtaag | 60 | |
| gttgccatcg ttggctacgg ctcccagggc cacgcacacg gccagaacct ccgcgattct | 120 | |
| ggcgttgagg ttgtcattgg tgagttcgag ggctccaagt ccgcagagaa ggcaaaggaa | 180 | |
| gcaggcttcg aagtcaagac caccgctgag gctgcagctt gggctgacgt catcatgctc | 240 | |
| ctggctccag acacctccca ggcagaaatc ttcaccaacg acatcgagcc aaacctgaac | 300 | |
| gcaggcgacg cactgctgtt cggccacggc ctgaacattc acttcgacct gatcaagcca | 360 | |
| gctgacgaca tcatcgttgg catggttgcg ccaaagggcc caggccactt ggttcgccgt | 420 | |

```
cagttcgttg atggcaaggg tgttccttgc ctcatcgcag tcgaccagga cccaaccgga      480
accgcacagg ctctgaccct gtcctacgca gcagcaatcg gtggcgcacg cgcaggcgtt      540
atcccaacca ccttcgaagc tgagaccgtc accgacctct tcggcgagca ggctgttctc      600
tgcggtggca ccgaggaact ggtcaaggtt ggcttcgagg ttctcaccga agctggctac      660
gagccagaga tggcatactt cgaggttctt cacgagctca agctcatcgt tgacctcatg      720
ttcgaaggtg gcatcagcaa catgaactac tctgtttctg acaccgctga gttcggtggc      780
tacctctccg gcccacgcgt catcgatgca gacaccaagt cccgcatgaa ggacatcctg      840
accgatatcc aggacggcac cttcaccaag cgcctcatcg caaacgttga gaacggcaac      900
accgagcttg agggtcttcg tgcttcctac aacaaccacc caatcgagga gaccggcgct      960
aagctccgcg acctcatgag ctgggtcaag gttgacgctc gcgcagaaac cgcttaa      1017
```

CORYNEFORM BACTERIUM TRANSFORMANT AND PROCESS FOR PRODUCING VALINE USING THE SAME

TECHNICAL FIELD

The present invention relates to a technique for producing valine. In more detail, the present invention relates to a coryneform bacterium transformant constructed by specific gene recombination and thereby provided with a valine-producing function, and relates to an efficient valine-producing process using the transformant.

BACKGROUND ART

Against the backdrop of global warming and exhaustion of fossil resources, production of chemical products using renewable resources, along with production of biofuels, is recognized as an emerging industry, biorefinery, which is an important means for realizing a low-carbon society, and has attracted keen attention.

Valine, which is one of the essential amino acids, is a useful substance as an ingredient of medicaments, foods, and cosmetics, or as an additive for animal feed, etc. Conventionally, valine is produced by a fermentation method or hydrolysis of proteins.

However, production of valine from renewable resources by a fermentation method is less productive as compared to production of lactic acid or ethanol for the reasons, for example, that the metabolic reaction from a raw material sugar consists of a great many steps and that produced valine causes feedback inhibition of metabolic enzymes, posing problems in industrial production.

Examples of known valine-producing technologies with the use of recombinant bacteria include the technologies described in Patent Literature 1 and 2.

Patent literature 1 discloses a technology for producing valine using a mutant strain of *Corynebacterium glutamicum* in which a gene encoding an enzyme involved in L-isoleucine biosynthesis, a gene encoding an enzyme involved in L-leucine biosynthesis, and a gene encoding an enzyme involved in D-pantothenic acid biosynthesis are weakened or deleted for an increased expression of a gene encoding an enzyme involved in L-valine biosynthesis.

Patent literature 2 discloses a technology for producing valine using a strain of *Corynebacterium* having an improved activity of transaminase C.

However, the processes of Non Patent Literature 1 and 2 do not have practically sufficient valine productivity.

CITATION LIST

Patent Literature

[PTL 1] JP 2009-521960 W
[PTL 2] JP 2008-514191 W

SUMMARY OF INVENTION

Technical Problem

An object of the present invention is to provide a microorganism capable of efficiently producing valine from a sugar, and a process for efficiently producing valine from a sugar.

Solution to Problem

A coryneform bacterium decomposes glucose into pyruvate through glycolysis. The coryneform bacterium further metabolizes the pyruvate into 2-acetolactate via acetohydroxy acid synthase, metabolizes the 2-acetolactate into 2,3-dihydroxyisovalerate via acetohydroxy acid isomeroreductase, metabolizes the 2,3-dihydroxyisovalerate into 2-ketoisovalerate in the presence of dihydroxy acid dehydratase, and metabolizes the 2-ketoisovalerate into valine via transaminase.

The present inventors found that a transformant constructed by introducing one or more of an acetohydroxy acid synthase gene consisting of the base sequence of SEQ ID NO: 37, an acetohydroxy acid isomeroreductase gene consisting of the base sequence of SEQ ID NO: 57, and a leucine dehydrogenase gene consisting of the base sequence of SEQ ID NO: 40 into a coryneform bacterium efficiently produces valine from a sugar as a raw material.

The DNA consisting of the base sequence of SEQ ID NO: 37 is a mutant of an acetohydroxy acid synthase gene (ilvBN gene) of *Corynebacterium glutamicum*, and the DNA consisting of the base sequence of SEQ ID NO: 57 is a mutant of an acetohydroxy acid isomeroreductase gene (ilvC gene) of *Corynebacterium glutamicum*.

The DNA consisting of the base sequence of SEQ ID NO: 40 encodes leucine dehydrogenase capable of catalyzing conversion of 2-ketoisovalerate into valine, which is usually catalyzed by transaminase in a coryneform bacterium. Whereas transaminase transfers an amino group from another amino acid to 2-ketoisovalerate, leucine dehydrogenase can transfer an amino group from inorganic $NH_4^+$ to 2-ketoisovalerate.

The inventors also found that the transformant can further efficiently produce valine in the case where the lactate dehydrogenase gene on the chromosome of the coryneform bacterium as the host is disrupted or deleted.

Further, the present inventors found that the transformant has a higher valine productivity when the growth is substantially arrested in a reaction mixture under reducing conditions as compared with the case when the growth is allowed in an aerobic reaction mixture.

The present invention, which has been completed based on the above-mentioned findings, provides the following transformant and process for producing valine.

[1] A transformant obtainable by introducing one or more of the following DNAs (a), (b), and (c) into a coryneform bacterium as a host.

(a) A DNA which encodes acetohydroxy acid synthase derived from *Corynebacterium glutamicum* and which has a mutation changing the glycine at position 156 to glutamic acid (G156E) in an amino acid sequence encoded by the DNA, or a DNA which hybridizes to a DNA consisting of a complementary base sequence of the DNA under stringent conditions and which encodes a polypeptide having acetohydroxy acid synthase activity.

(b) A DNA which encodes acetohydroxy acid isomeroreductase derived from *Corynebacterium glutamicum* and which has mutations changing the serine at position 34 to glycine (S34G), the leucine at position 48 to glutamic acid (L48E), and the arginine at position 49 to phenylalanine (R49F) in an amino acid sequence encoded by the DNA, or a DNA which hybridizes to a DNA consisting of a complementary base sequence of the DNA under stringent conditions and which encodes a polypeptide having acetohydroxy acid isomeroreductase activity.

(c) A DNA which encodes leucine dehydrogenase derived from *Lysinibacillus sphaericus*, or a DNA which hybridizes to a DNA consisting of a complementary base sequence of the DNA under stringent conditions and which encodes a polypeptide having leucine dehydrogenase activity.

[2] The transformant according to the above [1], wherein the DNA which encodes acetohydroxy acid synthase derived from *Corynebacterium glutamicum* and which has a mutation changing the glycine at position 156 to glutamic acid (G156E) in an amino acid sequence encoded by the DNA is a DNA consisting of the base sequence of SEQ ID NO: 37;
the DNA which encodes acetohydroxy acid isomeroreductase derived from *Corynebacterium glutamicum* and which has mutations changing the serine at position 34 to glycine (S34G), the leucine at position 48 to glutamic acid (L48E), and the arginine at position 49 to phenylalanine (R49F) in an amino acid sequence encoded by the DNA is a DNA consisting of the base sequence of SEQ ID NO: 57; and
the DNA which encodes leucine dehydrogenase derived from *Lysinibacillus sphaericus* is a DNA consisting of the base sequence of SEQ ID NO: 40.
[3] The transformant according to the above [1] or [2], wherein a DNA which encodes dihydroxy acid dehydratase derived from *Corynebacterium glutamicum* or a DNA which hybridizes to a DNA consisting of a complementary base sequence of the DNA under stringent conditions and which encodes a polypeptide having dihydroxy acid dehydratase activity is also introduced thereinto.
[4] The transformant according to any one of the above [1] to [3], wherein the lactase dehydrogenase gene of the coryneform bacterium as the host is disrupted or deleted.
[5] *Corynebacterium glutamicum* VAL4 (Accession Number: NITE BP-1122), which is a transformant of *Corynebacterium glutamicum*.
[6] A process for producing valine, which comprises a step of allowing the transformant of any one of the above [1] to [5] to react in a reaction mixture containing a sugar under reducing conditions, and a step of recovering valine from the reaction mixture.
[7] The process according to the above [6], wherein the transformant does not substantially grow in the reaction step.

Advantageous Effects of Invention

The transformant of the present invention is a coryneform bacterium having one or more of an acetohydroxy acid synthase gene of a specific sequence, an acetohydroxy acid isomeroreductase gene of a specific sequence, and a leucine dehydrogenase gene of a specific sequence, introduced thereinto, and therefore is capable of producing valine from a sugar more efficiently than conventional transformants do.

DESCRIPTION OF EMBODIMENTS

Figure 1:
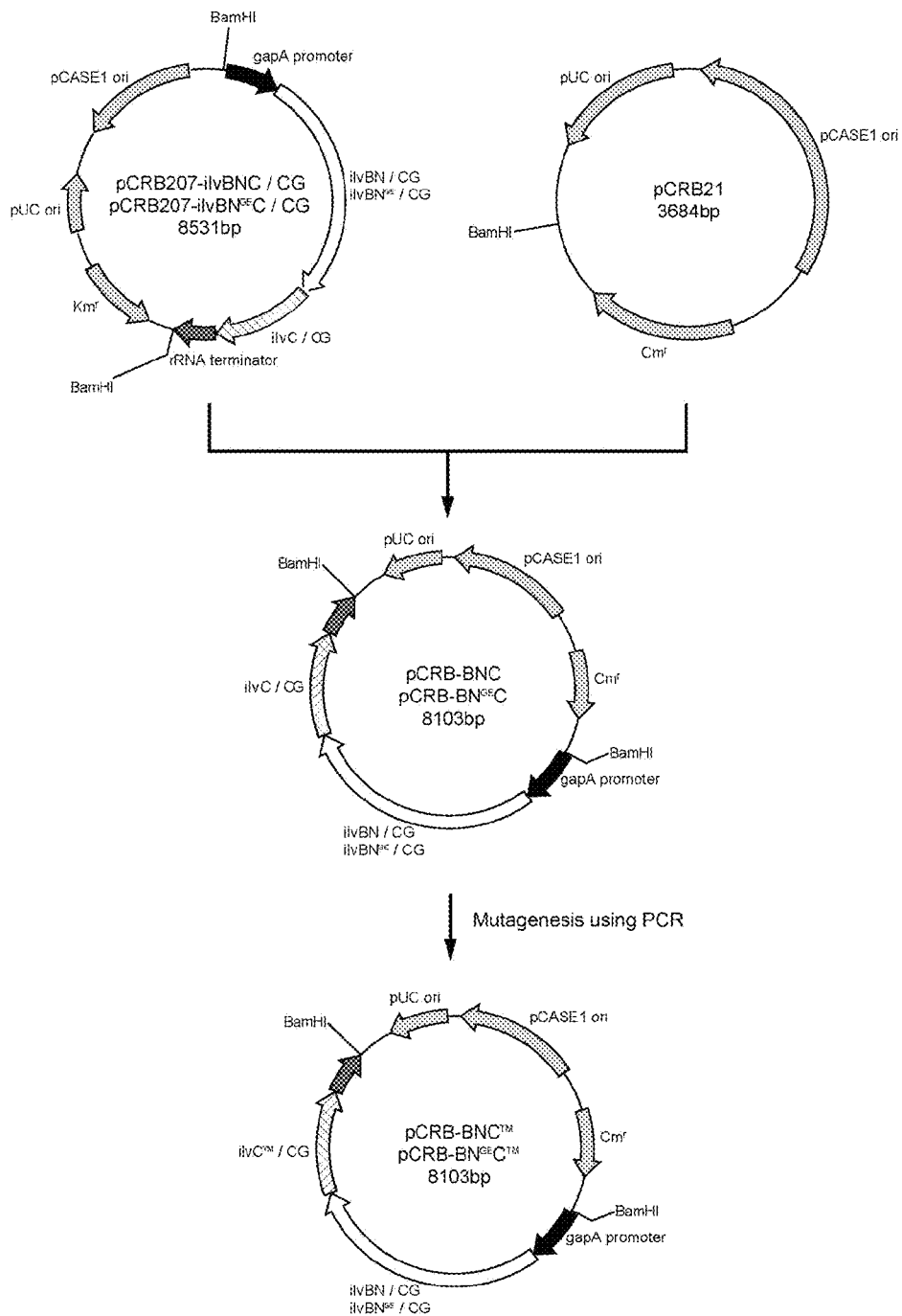
FIG. 1 shows the constructs of vectors used in Examples.

Hereinafter, the present invention will be described in detail.
(I) Transformant
Host
The coryneform bacterium is a group of microorganisms defined in Bergey's Manual of Determinative Bacteriology, Vol. 8, 599 (1974), and is not particularly limited as long as it grows under normal aerobic conditions. The specific examples include *Corynebacterium, Brevibacterium, Arthrobacter, Mycobacterium* and *Micrococcus*. Among the coryneform bacteria, *Corynebacterium* is preferred.
Examples of the *Corynebacterium* include *Corynebacterium glutamicum, Corynebacterium efficiens, Corynebacterium ammoniagenes, Corynebacterium halotolerance*, and *Corynebacterium alkanolyticum*.
Among them, *Corynebacterium glutamicum* is preferred for safety and high valine production. Examples of preferred strains include *Corynebacterium glutamicum* R (FERM P-18976), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (FERM BP-1497), and MJ-233AB-41 (FERM BP-1498). Among them, strains R (FERM P-18976), ATCC13032, and ATCC13869 are preferred.
According to molecular biological classification, names of some species of coryneform bacteria, such as *Brevibacterium flavum, Brevibacterium lactofermentum, Brevibacterium divaricatum*, and *Corynebacterium lilium* are standardized to *Corynebacterium glutamicum* (Liebl, W. et al., Transfer of *Brevibacterium divaricatum* DSM 20297T, "*Brevibacterium flavum*" DSM 20411, "*Brevibacterium lactofermentum*" DSM 20412 and DSM 1412, and *Corynebacterium glutamicum* and their distinction by rRNA gene restriction patterns. Int. J. Syst. Bacteriol. 41: 255-260. (1991); and Kazuo Komagata et al., "Classification of the coryneform group of bacteria", Fermentation and industry, 45: 944-963 (1987)).
*Brevibacterium lactofermentum* ATCC13869, *Brevibacterium flavum* MJ-233 (FERM BP-1497) and MJ-233AB-41 (FERM BP-1498), etc. of the old classification are also suitable as *Corynebacterium glutamicum*.
Examples of the *Brevibacterium* include *Brevibacterium ammoniagenes* (for example, ATCC6872).
Examples of the *Arthrobacter* include *Arthrobacter globiformis* (for example, ATCC8010, ATCC4336, ATCC21056, ATCC31250, ATCC31738 and ATCC35698).
Examples of the *Mycobacterium* include *Mycobacterium bovis* (for example, ATCC19210 and ATCC27289).
Examples of the *Micrococcus* include *Micrococcus freudenreichii* (for example, NO. 239 (FERM P-13221)), *Micrococcus leuteus* (for example, NO. 240 (FERM P-13222)), *Micrococcus ureae* (for example, IAM1010), and *Micrococcus roseus* (for example, IF03764).
The coryneform bacteria may be, let alone a wild strain, a mutant thereof or an artificial recombinant thereof. Examples thereof include disruptants in which a gene of lactate dehydrogenase, phosphoenolpyruvate carboxylase, or malate dehydrogenase is disrupted. Using such a disruptant as a host can improve valine productivity and reduce production of by-products.
Among them, preferred is a disruptant in which a lactate dehydrogenase gene is disrupted. In the disruptant, the lactate dehydrogenase gene is disrupted and the metabolic pathway from pyruvic acid to lactic acid is blocked. Particularly preferred is a disruptant of *Corynebacterium glutamicum* R (FERM P-18976) strain in which the lactate dehydrogenase gene is disrupted.
Such a disruptant can be prepared based on a conventional gene engineering process. Such a lactate dehydrogenase disruptant and the preparation process thereof are described in WO 2005/010182 A1.
Acetohydroxy Acid Synthase Gene (ilvBN Gene)
Acetohydroxy acid synthase is an enzyme that catalyzes the following reaction.

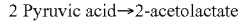

In the present invention, as an acetohydroxy acid synthase gene, a DNA of an acetohydroxy acid synthase gene derived from *Corynebacterium glutamicum*, which has a mutation changing the glycine at position 156 to glutamic acid (G156E) in an amino acid sequence encoded by the gene, can be used. In particular, a DNA consisting of the base sequence of SEQ ID NO: 37 is preferred.

Further, in the present invention, a DNA (analog) which hybridizes to a DNA consisting of a complementary base sequence of the DNA of an acetohydroxy acid synthase gene derived from *Corynebacterium glutamicum*, which has a mutation changing the glycine at position 156 to glutamic acid (G156E) in an amino acid sequence encoded by the gene, or a complementary base sequence of SEQ ID NO: 37 under stringent conditions and which encodes a polypeptide having acetohydroxy acid synthase activity can also be used.

The "stringent conditions" as used herein means general conditions, for example, the conditions described in Molecular Cloning, A Laboratory Manual, Second edition, 1989, Vol. 2, p. 11. 45. It means, in particular, conditions where hybridization occurs at a temperature 5 to 10° C. below the melting temperature (Tm) of a perfect hybrid.

Further, in the present invention, a DNA (analog) consisting of a base sequence which has 90% or more, preferably 95% or more, more preferably 98% or more of homology with a DNA which has a mutation changing the glycine at position 156 to glutamic acid (G156E) in an amino acid sequence encoded by the gene and which encodes a polypeptide having acetohydroxy acid synthase activity can also be used.

The base sequence homology was calculated using GENETYX Ver. 8 (made by Genetyx).

The acetohydroxy acid synthase activity can be determined by mixing 100 mM potassium phosphate (pH 7.5), 50 mM sodium pyruvate, 10 mM $MgCl_2$, 0.1 mM thiamine pyrophosphate, 0.1 mM flavin adenine dinucleotide, and an enzyme to be tested, and then measuring, as an index, the reduction in the absorbance of pyruvic acid at 333 nm ($\epsilon$=17.5/M·cm). Activity that produces 1 µmol of 2-acetolactic acid per minute is determined as 1 unit of acetohydroxy acid synthase activity.

Regarding an acetohydroxy acid synthase gene derived from *Corynebacterium glutamicum*, an analog of a DNA which has a mutation changing the glycine at position 156 to glutamic acid (G156E) in an amino acid sequence encoded by the gene or a DNA consisting of the base sequence of SEQ ID NO: 37 can be selected from a DNA library of a different species by, for example, PCR or hybridization using a primer or a probe designed based on these base sequences according to a conventional method, and as a result, a DNA which encodes a polypeptide having acetohydroxy acid synthase activity can be obtained with a high probability.

Acetohydroxy Acid Isomeroreductase Gene (ilvC Gene)

Acetohydroxy acid isomeroreductase is an enzyme that catalyzes the following reaction.

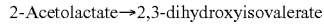

2-Acetolactate→2,3-dihydroxyisovalerate

In the present invention, as an acetohydroxy acid isomeroreductase gene, a DNA of an acetohydroxy acid isomeroreductase gene derived from *Corynebacterium glutamicum*, which has mutations changing the serine at position 34 to glycine (S34G), the leucine at position 48 to glutamic acid (L48E), and the arginine at position 49 to phenylalanine (R49F) in an amino acid sequence encoded by the gene, can be used. In particular, a DNA consisting of the base sequence of SEQ ID NO: 57 is preferred.

Further, in the present invention, as an acetohydroxy acid isomeroreductase gene derived from *Corynebacterium glutamicum*, a DNA (analog) which hybridizes to a DNA consisting of a complementary base sequence of a DNA having mutations changing the serine at position 34 to glycine (S34G), the leucine at position 48 to glutamic acid (L48E), and the arginine at position 49 to phenylalanine (R49F) in an amino acid sequence encoded by the gene or the base sequence of SEQ ID NO: 57 under stringent conditions and which encodes a polypeptide having acetohydroxy acid isomeroreductase activity can also be used.

Further, in the present invention, as an acetohydroxy acid isomeroreductase gene derived from *Corynebacterium glutamicum*, a DNA (analog) consisting of a base sequence which has 90% or more, preferably 95% or more, more preferably 98% or more of homology with a DNA having mutations changing the serine at position 34 to glycine (S34G), the leucine at position 48 to glutamic acid (L48E), and the arginine at position 49 to phenylalanine (R49F) in an amino acid sequence encoded by the gene or the base sequence of SEQ ID NO: 57 and which encodes a polypeptide having acetohydroxy acid isomeroreductase activity can also be used.

The acetohydroxy acid isomeroreductase activity can be determined by mixing 100 mM potassium phosphate (pH 7.5), 10 mM acetolactic acid, 5 mM $MgCl_2$, 0.2 mM NADPH, and an enzyme to be tested, and then measuring, as an index, the reduction in the absorbance of NADPH at 340 nm ($\epsilon$=6220/M·cm). Activity that produces 1 µmol of 2,3-dihydroxyisovaleric acid per minute is determined as 1 unit of acetohydroxy acid isomeroreductase activity.

Leucine Dehydrogenase Gene

In the present invention, a leucine dehydrogenase gene derived from *Lysinibacillus sphaericus* can be used. In particular, the DNA consisting of the base sequence of SEQ ID NO: 40 is preferred.

In the present invention, a DNA (analog) which hybridizes to a DNA consisting of a complementary base sequence of the leucine dehydrogenase gene (DNA) derived from *Lysinibacillus sphaericus* or the base sequence of SEQ ID NO: 40 under stringent conditions and which encodes a polypeptide having leucine dehydrogenase activity can also be used.

Further, in the present invention, a DNA (analog) consisting of a base sequence which has 90% or more, preferably 95% or more, more preferably 98% or more of homology with the base sequence of the leucine dehydrogenase gene (DNA) derived from *Lysinibacillus sphaericus* or the base sequence of SEQ ID NO: 40 and which encodes a polypeptide having leucine dehydrogenase activity can also be used.

The leucine dehydrogenase activity can be determined by mixing 100 mM glycine/NaOH (pH 9.5), 10 mM 2-ketoisovaleric acid, 200 mM ammonium chloride, 0.2 mMNADH, and an enzyme to be tested, and then measuring, as an index, the reduction in the absorbance of NADH at 340 nm ($\epsilon$=6220/M·cm). Activity that produces 1 µmol of valine per minute is determined as 1 unit of leucine dehydrogenase activity.

As described above, the transformant of the present invention is constructed by introducing one or more of the following genes (a) to (c) into a coryneform bacterium as a host.

(a) An acetohydroxy acid synthase gene derived from *Corynebacterium glutamicum*, which has a mutation changing the glycine at position 156 to glutamic acid (G156E) in an amino acid sequence encoded by the gene, or an analog thereof.

(b) An acetohydroxy acid isomeroreductase gene derived from *Corynebacterium glutamicum*, which has mutations changing the serine at position 34 to glycine (S34G), the leucine at position 48 to glutamic acid (L48E), and the arginine at position 49 to phenylalanine (R49F) in an amino acid sequence encoded by the gene, or an analog thereof.

(c) A leucine dehydrogenase gene derived from *Lysinibacillus sphaericus*, or an analog thereof.

The combination of transgenes may be any of combination of (a) and (b); combination of (a) and (c); combination of (b) and (c); and combination of (a), (b), and (c). Among them, the combination of (a), (b), and (c) is preferred.

Dihydroxy Acid Dehydratase Gene

In any case, it is preferred that a dihydroxy acid dehydratase gene (in particular, a DNA consisting of the base sequence of SEQ ID NO: 43) derived from *Corynebacterium glutamicum* or an analog thereof is also introduced into the host for further efficient valine production.

Examples of the analog include a DNA which hybridizes to a DNA consisting of a complementary base sequence of SEQ ID NO: 43 under stringent conditions and which encodes a polypeptide having dihydroxy acid dehydratase activity; and a DNA which has 90% or more, preferably 95% or more, more preferably 98% or more homology with the base sequence of SEQ ID NO: 43 and which encodes a polypeptide having dihydroxy acid dehydratase activity.

The dihydroxy acid dehydratase activity can be measured using the increase in absorbance at 340 nm associated with the increase in 2-ketoisovaleric acid formed from 2,3-dihydroxyisovaleric acid (Dennis H. F., et. al., The role and properties of the iron-sulfur cluster in *Escherichia coli* dihydroxyacid dehydratase. J. Biol. Chem., 268: 14732-14742 (1993)). As the reaction mixture for the activity measurement, a 50 mM tris-hydrochloric acid buffer solution at pH 8.0 with 10 mM magnesium chloride and 6 mM 2,3-dihydroxyisovaleric acid was used. To the reaction mixture, Enzyme Liquid 1 was added at 30° C. to start the reaction. From the difference of the slope of decrease in absorbance between the reaction mixture and a reaction mixture without 2,3-dihydroxyisovaleric acid, the activity value can be calculated using a molar absorbance coefficient of 190 $M^{-1}$ $cm^{-1}$.

Construction of Vector for Transformation

The DNA which encodes acetohydroxy acid synthase, the DNA which encodes acetohydroxy acid isomeroreductase, and the DNA which encodes leucine dehydrogenase are each amplified by PCR and then cloned into a suitable vector which is replicable in a host.

The plasmid vector may be any plasmid vector as long as it comprises a gene responsible for autonomously replicating function in a coryneform bacterium. Specific examples of the plasmid vector include pAM330 derived from *Brevibacterium lactofermentum* 2256 (JP 58-67699 A; Miwa, K. et al., Cryptic plasmids in glutamic acid-producing bacteria. Agric. Biol. Chem. 48:2901-2903 (1984); and Yamaguchi, R. et al., Determination of the complete nucleotide sequence of the *Brevibacterium lactofermentum* plasmid pAM330 and the analysis of its genetic information. Nucleic Acids Symp. Ser. 16:265-267 (1985)); pHM1519 derived from *Corynebacterium glutamicum* ATCC13058 (Miwa, K. et al., Cryptic plasmids in glutamic acid-producing bacteria. Agric. Biol. Chem. 48:2901-2903 (1984)) and pCRY30 derived from the same (Kurusu, Y. et al., Identification of plasmid partition function in coryneform bacteria. Appl. Environ. Microbiol. 57:759-764 (1991)); pCG4 derived from *Corynebacterium glutamicum* T250 (JP 57-183799 A; and Katsumata, R. et al., Protoplast transformation of glutamate-producing bacteria with plasmid DNA. J. Bacteriol., 159:306-311 (1984)), pAG1, pAG3, pAG14 and pAG50 derived from the same (JP 62-166890 A), and pEK0, pEC5 and pEKEx1 derived from the same (Eikmanns, B. J. et al., A family of *Corynebacterium glutamicum*/*Escherichia coli* shuttle vectors for cloning, controlled gene expression, and promoter probing. Gene, 102: 93-98 (1991)); etc.

Examples of a preferred promoter include promoter PgapA as a promoter of the glyceraldehyde-3-phosphate dehydrogenase A gene (gapA), promoter Pmdh as a promoter of the malate dehydrogenase gene (mdh), and promoter PldhA as a promoter of lactate dehydrogenase A gene (ldhA), all of which are derived from *Corynebacterium glutamicum* R, and among them, PgapA is preferred.

Examples of a preferred terminator include terminator rrnB T1T2 of *Escherichia coli* rRNA operon, terminator trpA of *Escherichia coli*, and terminator trp of *Brevibacterium lactofermentum*, and among them, terminator rrnB T1T2 is preferred.

Transformation

As a method of transformation, any publicly known method can be used without limitation. Examples of such a known method include the calcium chloride/rubidium chloride method, the calcium phosphate method, DEAE-dextran transfection, and electroporation. Among them, preferred for a coryneform bacterium is electroporation, which can be performed by a known method (Kurusu, Y. et al., Electroporation-transformation system for Coryneform bacteria by auxotrophic complementation, Agric. Biol. Chem. 54:443-447 (1990); and Vertes A. A. et al., Presence of mrr- and mcr-like restriction systems in Coryneform bacteria. Res. Microbiol. 144:181-185 (1993)).

The transformant is cultured using a culture medium usually used for culture of microorganisms. The culture medium may be a natural or synthetic medium containing a carbon source, a nitrogen source, inorganic salts, other nutritional substances, etc.

Examples of the carbon source include carbohydrates and sugar alcohols such as glucose, fructose, sucrose, mannose, maltose, mannitol, xylose, arabinose, galactose, starch, molasses, sorbitol and glycerol; organic acids such as acetic acid, citric acid, lactic acid, fumaric acid, maleic acid and gluconic acid; and alcohols such as ethanol and propanol. Hydrocarbons, such as normal paraffin, etc. may also be used as desired. These carbon sources may be used alone or as a mixture of two or more thereof. The concentration of these carbon sources in the culture medium is usually about 0.1 to 10 w/v %.

Examples of the nitrogen source include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %.

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %. Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 5 to 8.

Examples of the preferable microbial culture medium include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc.

The culture temperature is about 15 to 45° C., and the culture period is about 1 to 7 days.

Disruption or Deletion in Host Chromosomal Gene

As described above, in the coryneform bacterium as a host, one or more of the lactate dehydrogenase gene, the phosphoenolpyruvate carboxylase gene, the pyruvate carboxylase gene, and the maleate dehydrogenase gene preferably are disrupted or deleted for further efficient valine production.

Replacement of a gene on the chromosome with the corresponding gene having an disruption or deletion can be achieved by creating a gene with deletion mutation for not allowing production of a normally functioning enzyme protein, and transforming a bacterium with a DNA comprising the mutated gene for recombination in which the gene on the chromosome and the mutated gene are exchanged. An enzyme protein encoded by a gene having a disruption or deletion, even when produced, has a conformation different from that of the wild type, and has no or reduced function. The gene deletion or gene disruption by way of gene replacement through such homologous recombination has already been established, and examples thereof include a method using a plasmid containing a temperature sensitive replication origin or a plasmid capable of conjugal transfer, and a method using a suicide vector not having a replication origin that works in a host (U.S. Pat. No. 6303383 and JP 05-007491 A).

Specifically, for example, a coryneform bacterium in which the lactate dehydrogenase gene is disrupted or deleted can be obtained by the method described in J. Mol. Microbiol. Biotechnol., Vol. 8, 243-254 (2004).

(II) Process for Producing Valine

Valine can be produced by a process comprising a step of allowing the above-described transformant of the present invention to react in a reaction mixture containing a sugar under reducing conditions, and a step of recovering valine from the reaction mixture.

Growth of Microorganism

Before the reaction, the transformant is preferably cultured and grown under aerobic conditions at about 25 to 38° C. for about 12 to 48 hours.

Culture Medium

The culture medium used for aerobic culture of the transformant before the reaction may be a natural or synthetic medium containing a carbon source, a nitrogen source, inorganic salts, other nutritional substances, etc.

Examples of the carbon source that can be used include sugars (monosaccharides such as glucose, fructose, mannose, xylose, arabinose, and galactose; disaccharides such as sucrose, maltose, lactose, cellobiose, xylobiose, and trehalose; polysaccharides such as starch; and molasses); sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin.

These carbon sources may be used alone or as a mixture of two or more thereof.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %.

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 6 to 8.

Specific examples of the preferable culture medium for coryneform bacteria include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc. Such a culture medium can be used after prepared so as to contain a sugar at a concentration in the above-mentioned range.

Reaction Mixture

The reaction mixture may be a natural or synthetic reaction mixture containing a carbon source, a nitrogen source, inorganic salts, other nutritional substances, etc.

As the carbon source, a sugar is used. Examples of the sugar include monosaccharides such as glucose, fructose, mannose, xylose, arabinose, and galactose; disaccharides such as sucrose, maltose, lactose, cellobiose, xylobiose, and trehalose; polysaccharides such as starch; and molasses. In addition, a saccharified liquid which is obtainable by saccharifying non-edible agricultural waste including rice straw, bagasse, and corn stover; or energy crops including switchgrass, napier grass, and *Miscanthus* and which contains two or more kinds of sugars, such as glucose, xylose, etc., can also be used. Among them, monosaccharides are preferred, and glucose is more preferred. In addition, glucose-containing sugars (disaccharides, oligosaccharides, and polysaccharides) are also preferred.

As the carbon source, besides sugars, sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin can also be used.

These carbon sources may be used alone or as a mixture of two or more thereof.

The concentration of the sugar in the reaction mixture is preferably about 1 to 20 w/v %, more preferably about 2 to 10 w/v %, and still more preferably about 2 to 5 w/v %.

The total concentration of the carbon sources including the sugar in the reaction mixture is usually about 2 to 5 w/v %.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the reaction mixture varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the reaction mixture varies depending on the kind of the inorganic salts, but is usually about 0.01 to 1 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the reaction mixture is preferably about 6 to 8.

Specific examples of the preferable culture medium for coryneform bacteria include the above-mentioned BT medium, etc. Such a culture medium can be used after prepared so as to contain a sugar at a concentration in the above-mentioned range.

Reaction Conditions

The reaction temperature, that is, the temperature for keeping the transformant alive during the reaction is preferably about 20 to 50° C., and more preferably about 25 to 47° C. When the temperature is in the above range, valine can be efficiently produced.

The reaction period is preferably about 1 to 7 days, and more preferably about 1 to 3 days.

The culture may be a batch process, a fed-batch process, or a continuous process. Among them, a batch process is preferred.

The reaction may be performed under aerobic conditions or reducing conditions.

<Reducing Conditions>

Under reducing conditions, coryneform bacteria do not substantially grow and can further efficiently produce valine.

The "reducing conditions" is defined based on the oxidation-reduction potential of the reaction mixture. The oxidation-reduction potential of the reaction mixture is preferably about −200 mV to −500 mV, and more preferably about −250 mV to −500 mV.

The reducing conditions of the reaction mixture can be simply estimated with the use of resazurin indicator (in reducing conditions, decolorization from blue to colorless is observed). However, for precise measurement, a redox-potential meter (for example, ORP Electrodes made by BROADLEY JAMES) is used.

As a method of preparing a reaction mixture under reducing conditions, any publicly known method can be used without limitation. For example, as a liquid medium for preparation of the reaction mixture, an aqueous solution for a reaction mixture may be used instead of distilled water or the like. As reference for preparation of the aqueous solution for a reaction mixture, for example, the method for preparing a culture medium for strictly anaerobic microorganisms, such as sulfate-reducing microorganisms (Pfennig, N. et al.: The dissimilatory sulfate-reducing bacteria, In The Prokaryotes, A Handbook on Habitats, Isolation and Identification of Bacteria, Ed. by Starr, M. P. et al. Berlin, Springer Verlag, 926-940, 1981, or Nogeikagaku Jikkensho, Ed. by Kyoto Daigaku Nogakubu Nogeikagaku Kyoshitsu, Vol. 3, Sangyo Tosho, 1990, Issue 26) may be used, and such a method provides an aqueous solution under desired reducing conditions.

Specifically, by treating distilled water or the like with heat or under reduced pressure for removal of dissolved gases, an aqueous solution for a reaction mixture under reducing conditions can be obtained. In this case, for removal of dissolved gases, especially dissolved oxygen, distilled water or the like may be treated under reduced pressure of about 10 mmHg or less, preferably about 5 mmHg or less, more preferably about 3 mmHg or less, for about 1 to 60 minutes, preferably for about 5 to 40 minutes.

Alternatively, by adding a suitable reducing agent (for example, thioglycolic acid, ascorbic acid, cysteine hydrochloride, mercaptoacetic acid, thiol acetic acid, glutathione, sodium sulfide, etc.), an aqueous solution for a reaction mixture under reducing conditions can be prepared.

These methods may be suitably combined to prepare an effective aqueous solution for a reaction mixture under reducing conditions.

It is preferred to maintain the reducing conditions of the reaction mixture during the reaction. For maintenance of reducing conditions, it is preferred that oxygen from the outside of the reaction system is prevented to the utmost extent from entering the system. Specific examples of the method employed for this purpose include a method comprising encapsulating the reaction system with inert gas, such as nitrogen gas, carbon dioxide gas, etc. In some cases, for allowing the metabolic functions in the cells of the aerobic bacterium of the present invention to work effectively during the reaction, addition of a solution of various nutrients or a reagent solution for adjusting and maintaining the pH of the reaction system may be needed. In such a case, for more effective prevention of oxygen incorporation, it is effective to remove oxygen in the solutions to be added, in advance.

Recovery of Valine

Through the culture performed in the above manner, valine is produced in the reaction mixture. Valine can be recovered by collecting the reaction mixture, and it is also feasible to isolate valine from the reaction mixture by a known method. Examples of such a known method include an ion-exchange resin method, a concentration method, a crystallization method, an activated carbon adsorption elution method, etc.

EXAMPLES

Hereinafter, the present invention will be described in more detail by way of Examples, but the present invention is not limited thereto.

Example 1

Cloning of Mutated Acetohydroxy Acid Synthase Gene (1) Preparation of Valine Analog Resistant Strain

*Corynebacterium glutamicum* R was exposed to 300 µg/mL of N-methyl-N'-nitro-N-nitrosoguanidine at 30° C. for 1 hour, and then cultured in A Medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, and 7 g of vitamin assay casamino acid were dissolved in 1 L of distilled water) until the concentration became about $10^9$ cells/mL. The bacterial cells were collected, washed with a minimal medium (BT medium), and then applied onto a BT plate medium containing 4% glucose and 4% DL-α-aminobutyrate, which is a valine analog, to be cultured at 30° C. for 5 days.

The mutant strain grown on the plate medium containing the valine analog was inoculated into a test tube containing 10 mL of A liquid medium and was aerobically cultured with shaking at 33° C. for 16 hours. The cultured bacterial cells were collected by centrifugation (14,500 rpm at 4° C. for 2 minutes), washed with 2 mL of BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), and suspended in 1 mL of BT medium. Subsequently, the cells in the suspension were inoculated into 10 mL of BT medium so that the final concentration was $OD_{610}$=0.1, and were aerobically cultured with shaking at 33° C. for 48 hours Then, screening for a strain having high L-valine productivity was performed.

For quantitative determination of valine, the culture medium was sampled and centrifuged (14,500 rpm at 4° C. for 1 minute), and the obtained supernatant was analyzed by an amino acid analysis system (Prominence, made by Shimadzu). The analysis conditions are shown in Table 1 below.

TABLE 1

Measurement conditions of amino acid analysis system

| | |
|---|---|
| Guard column | ISC-30/S0504 (Na) |
| Column for amino acid analysis | Shim-pack VP-ODS |
| Mobile phase | Amino acid mobile phase kit (Na type) |
| Column temperature | 60° C. |
| Flow rate | 0.6 mL/min |
| Detection | Spectrofluorometric detector (RF-10$A_{XL}$) |

(2) Cloning and Base Sequence Determination of Mutated Acetohydroxy Acid Synthase Gene To extract chromosomal DNA from the obtained mutant having high valine productivity, the bacterium was inoculated, with the use of a platinum loop, into A Medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, and 7 g of vitamin assay casamino acid were dissolved in 1 L of distilled water), which was supplemented with 50% (w/v) glucose as a carbon source to a final concentration of 4%, and cultured with shaking at 33° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

Sequence analysis of the acetohydroxy acid synthase gene using the obtained chromosomal DNA revealed that the glycine at position 156 was replaced with glutamic acid.

Example 2

Cloning and Expression of Valine-Producing Genes (1) Extraction of Chromosomal DNA from Microorganisms To extract chromosomal DNA from *Corynebacterium glutamicum* R (FERM P-18976), the bacterium was inoculated, with the use of a platinum loop, into A medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, and 7 g of vitamin assay casamino acid were dissolved in 1 L of distilled water), which was supplemented with 50% (w/v) glucose as a carbon source to a final concentration of 4%, and cultured with shaking at 33° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Lysinibacillus sphaericus* NBRC 3525, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

(2) Construction of Cloning Vectors

Construction of Cloning Vector pCRB21

A DNA fragment comprising a DNA replication origin sequence of pCASE1, a plasmid derived from *Corynebacterium casei* JCM12072 (hereinafter abbreviated as pCASE1-ori) and a DNA fragment comprising a cloning vector pHSG398 (made by Takara Bio, Inc.) were amplified by the following PCR method.

In the PCR, the following sets of primers were synthesized based on SEQ ID NO: 1 (pCASE1-ori sequence) and SEQ ID NO: 2 (cloning vector pHSG398) for cloning of the pCASE1-ori sequence and the cloning vector pHSG398, and were used.

Primers for pCASE1-Ori Sequence Amplification

```
(a-1);
                                            (SEQ ID NO: 3)
5'-GGCAG AGATCT AGAACGTCCGTAG-3'

(b-1);
                                            (SEQ ID NO: 4)
5'-CGGAA AGATCT GACTTGGTTACGATG-3'
```

Primers (a-1) and (b-1) each have a BglII restriction enzyme site added thereto.

Primers for cloning vector pHSG398 amplification (a-2):
(SEQ ID NO: 5)
5'-CAGTGG AGATCT GTCGAACGGAAG-3'

(b-2):
(SEQ ID NO: 6)
5'-CCGTT AGATCT AGTTCCACTGAGC-3'

Primers (a-2) and (b-2) each have a BglII restriction enzyme site added thereto.

As the template DNA, total DNA extracted from *Corynebacterium casei* JCM12072 obtained from Japan Collection of Microorganisms (JCM) and cloning vector pHSG398 (made by Takara Bio, Inc.) were used.

Actual PCR was performed with the use of a Veriti thermal cycler (made by Applied Biosystems) and PrimeSTAR HS DNA Polymerase (made by Takara Bio, Inc.) as a reaction reagent under the conditions described below.

Reaction Mixture:

| | |
|---|---|
| PrimeSTAR HS DNA Polymerase ™ (2.5 U/μL) | 0.5 μL |
| 5 X PrimeSTAR Buffer (Mg$^{2+}$ plus) | 10 μL |
| dNTP Mixture (2.5 mM each) | 4 μL |
| Template DNA | 5 μL (DNA content: 1 μg or less) |
| The above 2 primers*⁾ | 0.5 μL each (final conc.: 1 μM) |
| Sterile distilled water | 29.5 μL |

The above ingredients were mixed, and 50 μL of the reaction mixture was subjected to PCR.
*⁾For amplification of the pCASE1-ori sequence, a combination of primers (a-1) and (b-1), and for amplification of the cloning vector pHSG398, a combination of primers (a-2) and (b-2) were used.

PCR Cycle:
  Denaturation step: 94° C., 60 seconds
  Annealing step: 52° C., 60 seconds
  Extension step: 72° C.
  pCASE1-ori sequence: 87 seconds
  Cloning vector pHSG398: 134 seconds
  A cycle consisting of the above 3 steps was repeated 30 times.

Using 10 μL of the above-produced reaction mixture, 0.8% agarose gel electrophoresis was performed. In the case of the pCASE1-ori sequence, an about 1.5-kb DNA fragment was detected. In the case of the cloning vector pHSG398, an about 2.2-kb DNA fragment was detected.

10 μL of the about 1.5-kb DNA fragment comprising the pCASE1-ori sequence derived from *Corynebacterium casei*, and 10 μL of the about 2.2-kb DNA fragment comprising the cloning vector pHSG398, both amplified by the above PCR, were each cut with the use of restriction enzyme BglII and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid A.

With the use of the Ligation Liquid A, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of chloramphenicol.

A growing strain on the culture medium was subjected to liquid culture in the usual manner. Plasmid DNA was extracted from the culture and cut with the use of restriction enzyme BglII to confirm the inserted fragment. As a result, in addition to an about 2.2-kb DNA fragment of the cloning vector pHSG398, an about 1.5-kb DNA fragment of the pCASE-ori sequence was confirmed.

The cloning vector comprising the pCASE1-ori sequence was named pCRB21.

Construction of Cloning Vector pCRB22

A DNA fragment comprising a DNA replication origin sequence of pCASE1, a plasmid derived from *Corynebacterium casei* JCM12072 (hereinafter abbreviated as pCASE1-ori) and a DNA fragment comprising a cloning vector pHSG298 (made by Takara Bio, Inc.) were amplified by the following PCR method.

In the PCR, the following sets of primers were synthesized based on SEQ ID NO: 7 (pCASE1-ori sequence) and SEQ ID NO: 8 (cloning vector pHSG298) for cloning of the pCASE1-ori sequence and the cloning vector pHSG298, and were used.

Primers for pCASE1-Ori Sequence Amplification (a-3);
(SEQ ID NO: 9)
5'-GGCAG AGATCT AGAACGTCCGTAG-3'

(b-3);
(SEQ ID NO: 10)
5'-CGGAA AGATCT GACTTGGTTACGATG-3'

Primers (a-3) and (b-3) each have a BglII restriction enzyme site added thereto.

Primers for Cloning Vector pHSG298 Amplification (a-4):
(SEQ ID NO: 11)
5'-GCTGG AGATCT AGGTTTCCCGAC-3'

(b-4):
(SEQ ID NO: 12)
5'-GGGAA AGATCT CGTGCCAGCTGC-3'

Primers (a-4) and (b-4) each have a BglII restriction enzyme site added thereto.

As the template DNA, total DNA extracted from *Corynebacterium casei* JCM12072 obtained from Japan Collection of Microorganisms (JCM) and cloning vector pHSG298 (made by Takara Bio, Inc.) were used.

Actual PCR was performed with the use of a Veriti thermal cycler (made by Applied Biosystems) and PrimeSTAR HS DNA Polymerase (made by Takara Bio, Inc.) as a reaction reagent under the conditions described below.

Reaction Mixture:

| | |
|---|---|
| PrimeSTAR HS DNA Polymerase ™ (2.5 U/μL) | 0.5 μL |
| 5 X PrimeSTAR Buffer (Mg$^{2+}$ plus) | 10 μL |
| dNTP Mixture (2.5 mM each) | 4 μL |
| Template DNA | 5 μL (DNA content: 1 μg or less) |
| The above 2 primers*⁾ | 0.5 μL each (final conc.: 1 μM) |
| Sterile distilled water | 29.5 μL |

The above ingredients were mixed, and 50 μL of the reaction mixture was subjected to PCR.
*⁾For amplification of the pCASE1-ori sequence, a combination of primers (a-3) and (b-3), and for amplification of the cloning vector pHSG298, a combination of primers (a-4) and (b-4) were used.

PCR Cycle:
  Denaturation step: 94° C., 60 seconds
  Annealing step: 52° C., 60 seconds
  Extension step: 72° C.
  pCASE1-ori sequence: 150 seconds
  Cloning vector pHSG298: 180 seconds A cycle consisting of the above 3 steps was repeated 30 times.

Using 10 µL of the above-produced reaction mixture, 0.8% agarose gel electrophoresis was performed. In the case of the pCASE1-ori sequence, an about 1.4-kb DNA fragment was detected. In the case of the cloning vector pHSG298, an about 2.7-kb DNA fragment was detected.

10 µL of the about 1.4-kb DNA fragment comprising the pCASE1-ori sequence derived from *Corynebacterium casei*, and 10 µL of the about 2.7-kb DNA fragment comprising the cloning vector pHSG298, both amplified by the above PCR, were each cut with the use of restriction enzyme BglII and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. This was named Ligation Liquid B.

With the use of the Ligation Liquid B, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut with the use of restriction enzyme BglII to confirm the inserted fragment. As a result, in addition to an about 2.7-kb DNA fragment of the cloning vector pHSG298, an about 1.4-kb DNA fragment of the pCASE-ori sequence was confirmed.

The cloning vector comprising the pCASE1-ori sequence was named pCRB22.

Construction of Cloning Vector pCRB12

A DNA fragment comprising a DNA replication origin sequence of pCG1 (JP 57-134500 A), which is a plasmid replicable in *Corynebacterium glutamicum* (hereinafter abbreviated as pCG1-ori) and a DNA fragment comprising a cloning vector pHSG298 (made by Takara Bio, Inc.) were amplified by the following PCR method.

In the PCR, the following sets of primers were synthesized based on SEQ ID NO: 13 (pCG1-ori sequence) and SEQ ID NO: 14 (cloning vector pHSG298) for cloning of the pCG1-ori sequence and the cloning vector pHSG298, and were used.

Primers for pCG1-Ori Sequence Amplification

```
(a-5):
                                       (SEQ ID NO: 15)
5'-GCGAA AGATCT AGCATGGTCGTC-3'

(b-5):
                                       (SEQ ID NO: 16)
5'-GTGAGC AGATCT GGAACCGTTATC-3'
```

Primers (a-5) and (b-5) each have a BglII restriction enzyme site added thereto.

Primers for Cloning Vector pHSG298 Amplification

```
(a-6):
                                       (SEQ ID NO: 17)
5'-GCTGG AGATCT AGGTTTCCCGAC-3'

(b-6):
                                       (SEQ ID NO: 18)
5'-GGGAA AGATCT CGTGCCAGCTGC-3'
```

Primers (a-6) and (b-6) each have a BglII restriction enzyme site added thereto.

As the template DNA, pCG1 (JP 57-134500 A) and cloning vector pHSG298 (made by Takara Bio, Inc.) were used.

Actual PCR was performed with the use of a Veriti thermal cycler (made by Applied Biosystems) and PrimeSTAR HS DNA Polymerase (made by Takara Bio, Inc.) as a reaction reagent under the conditions described below.

Reaction Mixture:

| | |
|---|---|
| PrimeSTAR HS DNA Polymerase ™ (2.5 U/µL) | 0.5 µL |
| 5 X PrimeSTAR Buffer (Mg²⁺ plus) | 10 µL |
| dNTP Mixture (2.5 mM each) | 4 µL |
| Template DNA | 5 µL (DNA content: 1 µg or less) |
| The above 2 primers*⁾ | 0.5 µL each (final conc.: 1 µM) |
| Sterile distilled water | 29.5 µL |

The above ingredients were mixed, and 50 µL of the reaction mixture was subjected to PCR.
*⁾For amplification of the pCG1-ori sequence, a combination of primers (a-5) and (b-5), and for amplification of the cloning vector pHSG298, a combination of primers (a-6) and (b-6) were used.

PCR Cycle:
  Denaturation step: 94° C., 60 seconds
  Annealing step: 52° C., 60 seconds
  Extension step: 72° C.
  pCG1-ori sequence: 113 seconds
  Cloning vector pHSG298: 127 seconds A cycle consisting of the above 3 steps was repeated 30 times.

Using 10 µL of the above-produced reaction mixture, 0.8% agarose gel electrophoresis was performed. In the case of the pCG1-ori sequence, an about 1.9-kb DNA fragment was detected. In the case of the cloning vector pHSG298, an about 2.7-kb DNA fragment was detected.

10 µL of the about 1.9-kb DNA fragment comprising the pCG1-ori sequence derived from pCG1, and 10 µL of the about 2.7-kb DNA fragment comprising the cloning vector pHSG298, both amplified by the above PCR, were each cut with the use of restriction enzyme BglII and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. This was named Ligation Liquid C.

With the use of the Ligation Liquid C, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut with the use of restriction enzyme BglII to confirm the inserted fragment. As a result, in addition to an about 2.7-kb DNA fragment of the cloning vector pHSG298, an about 1.9-kb DNA fragment of the pCG1-ori sequence was confirmed.

The cloning vector comprising the pCG1-ori sequence was named pCRB12.

Construction of Cloning Vector pCRB207

A DNA fragment comprising a promoter sequence of the gapA gene encoding the glyceraldehyde-3-phosphate dehydrogenase (hereinafter abbreviated as PgapA) derived from *Corynebacterium glutamicum* R, and a DNA fragment comprising an rrnBT1T2 bidirectional terminator sequence (hereinafter abbreviated as terminator sequence) derived from a cloning vector pKK223-3 (made by Pharmacia) were amplified by the following method.

In the PCR, the following sets of primers were synthesized based on SEQ ID NO: 19 (PgapA sequence) and SEQ ID NO: 20 (terminator sequence) for cloning of the PgapA sequence and the terminator sequence, and were used.

Primers for PgapA Sequence Amplification

```
(a-7);
                                      (SEQ ID NO: 21)
5'-CTCT GTCGAC CCGAAGATCTGAAGATTCCTG-3'

(b-7);
                                      (SEQ ID NO: 22)
5'-CTCT GTCGAC GGATCC CCATGG

TGTGTCTCCTCTAAAGATTGTAGG-3'
```

Primer (a-7) has a SalI restriction enzyme site added thereto, and primer (b-7) has SalI, BamHI, and NcoI restriction enzyme sites added thereto.

Primers for Terminator Sequence Amplification

```
(a-8);
                                      (SEQ ID NO: 23)
5'-CTCT GCATGC CCATGG CTGTTTTGGCGGATGAGAGA-3'

(b-8);
                                      (SEQ ID NO: 24)
5'-CTCT GCATGC TCATGA AAGAGTTTGTAGAAACGCAAAAAGG-3'
```

Primer (a-8) has SphI and NcoI restriction enzyme sites added thereto, and primer (b-8) has SphI and BspHI restriction enzyme sites added thereto.

As the template DNA, the chromosomal DNA extracted from *Corynebacterium glutamicum* R (FERM P-18976) and the plasmid pKK223-3 (made by Pharmacia) were used.

Actual PCR was performed with the use of a Veriti thermal cycler (made by Applied Biosystems) and PrimeSTAR HS DNA Polymerase (made by Takara Bio, Inc.) as a reaction reagent under the conditions described below.

Reaction Mixture:

| | |
|---|---|
| PrimeSTAR HS DNA Polymerase ™ (2.5 U/μL) | 0.5 μL |
| 5 X PrimeSTAR Buffer (Mg$^{2+}$ plus) | 10 μL |
| dNTP Mixture (2.5 mM each) | 4 μL |
| Template DNA | 5 μL (DNA content: 1 μg or less) |
| The above 2 primers*⁾ | 0.5 μL each (final conc.: 1 μM) |
| Sterile distilled water | 29.5 μL |

The above ingredients were mixed, and 50 μL of the reaction mixture was subjected to PCR.
*⁾For amplification of the PgapA sequence, a combination of primers (a-7) and (b-7), and for amplification of the terminator sequence, a combination of primers (a-8) and (b-8) were used.

PCR Cycle:
  Denaturation step: 94° C., 60 seconds
  Annealing step: 52° C., 60 seconds
  Extension step: 72° C.
  PgapA sequence: 45 seconds
  Terminator sequence: 30 seconds
  A cycle consisting of the above 3 steps was repeated 30 times.

Using 10 μL of the above-produced reaction mixture, 0.8% agarose gel electrophoresis was performed. In the case of the PgapA sequence, an about 0.6-kb DNA fragment was detected. In the case of the terminator sequence, an about 0.4-kb DNA fragment was detected.

10 μL of the about 0.6-kb DNA fragment comprising the PgapA sequence derived from *Corynebacterium glutamicum* R, which was amplified by the above PCR, and the about 4.1-kb cloning vector pCRB22 were each cut with the use of restriction enzyme SalI and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid D.

With the use of the Ligation Liquid D, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme SalI to confirm the inserted fragment. As a result, in addition to an about 4.1-kb DNA fragment of the cloning vector pCRB22, an about 0.6-kb DNA fragment of the PgapA sequence was confirmed.

The cloning vector comprising the PgapA sequence was named pCRB206.

10 μL of the about 0.4-kb DNA fragment comprising the terminator sequence derived from the plasmid pKK223-3, which was amplified by the above PCR, was cut with the use of restriction enzymes NcoI and BspHI, 2 μL of the above cloning vector pCRB206 was cut with the use of restriction enzyme NcoI, and both were processed at 70° C. for 10 minutes for deactivation of the restriction enzymes. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid E.

With the use of the Ligation Liquid E, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of the restriction enzyme to confirm the inserted fragment. As a result, in addition to an about 4.7-kb DNA fragment of the cloning vector pCRB206, an about 0.4-kb DNA fragment of the terminator sequence was confirmed.

The cloning vector comprising the rrnBT1T2 terminator sequence was named pCRB207.

(3) Cloning of Valine-Producing Genes

Cloning of Valine-Producing Genes Derived from *Corynebacterium glutamicum*

A DNA fragment comprising the ilvBN gene which encodes acetohydroxy acid synthase, a DNA fragment comprising the ilvC gene which encodes acetohydroxy acid isomeroreductase, a DNA fragment comprising the ilvD gene which encodes dihydroxy acid dehydratase, and a DNA fragment comprising the ilvE gene which encodes transaminase, all of which are derived from *Corynebacterium glutamicum*, were amplified by the PCR method as described below.

In the PCR, the following sets of primers were synthesized based on SEQ ID NO: 25 (the ilvBN gene of *Corynebacterium glutamicum*), SEQ ID NO: 26 (the ilvC gene of *Corynebacterium glutamicum*), SEQ ID NO: 27 (the ilvD gene of *Corynebacterium glutamicum*), and SEQ ID NO: 28 (the ilvE gene of *Corynebacterium glutamicum*) with the use of "394 DNA/RNA Synthesizer" made by Applied Biosystems for cloning of the ilvBN gene, the ilvC gene, the ilvD gene, and the ilvE gene, and were used.

Primers for ilvBN Gene Amplification

```
(a-9);
                                    (SEQ ID NO: 29)
5'-CTCT TCATGA ATGTGGCAGCTTCTCAAC-3'

(b-9);
                                    (SEQ ID NO: 30)
5'-CTCT TCATGA TTAGATCTTGGCCGGAGC-3'
```

Primers (a-9) and (b-9) each have a BspHI restriction enzyme site added thereto.

Primers for ilvC Gene Amplification

```
(a-10);
                                    (SEQ ID NO: 31)
5'-CTCT CCATGG CTATTGAACTGCTTTATGATG-3'

(b-10);
                                    (SEQ ID NO: 32)
5'-CTCT CCATGG AGATCTTTAAGCGGTTTCTGCGCGA-3'
```

Primers (a-10) and (b-10) each have an NcoI restriction enzyme site added thereto.

Primers for ilvD Gene Amplification

```
(a-11);
                                    (SEQ ID NO: 33)
5'-GA CCCGGG GAGCAGATTTGAAAAGCGCATCATG-3'

(b-11);
                                    (SEQ ID NO: 34)
5'-GA CCCGGG GGTACC GTATTTGCAACGGGGAGCTCCACCA-3'
```

Primer (a-11) has a SmaI restriction enzyme site added thereto, and primer (b-11) has SmaI and KpnI restriction enzyme sites added thereto.

Primers for ilvE Gene Amplification

```
(a-12);
                                    (SEQ ID NO: 35)
5'-GA CCCGGG CATCCCATAAAATGGGCTGACTAG-3'

(b-12);
                                    (SEQ ID NO: 36)
5'-GA CCCGGG GAGCTC CCCTGACTCCACCCCCTACGTCTCA-3'
```

Primer (a-12) has a SmaI restriction enzyme site added thereto, and primer (b-12) has SmaI and SacI restriction enzyme sites added thereto.

Cloning of Valine-Producing Gene Derived from *Corynebacterium glutamicum* Mutant Having High Valine Productivity A DNA fragment comprising the ilvBN gene which encodes acetohydroxy acid synthase derived from the *Corynebacterium glutamicum* mutant having high valine productivity was amplified by the PCR method as described below.

In the PCR, the following set of primers was synthesized based on SEQ ID NO: 37 (the mutated ilvBN gene of *Corynebacterium glutamicum*) with the use of "394 DNA/RNA Synthesizer" made by Applied Biosystems for cloning of the mutated ilvBN gene, and was used.

Primers for Mutated ilvBN Gene Amplification

```
(a-13):
                                    (SEQ ID NO: 38)
5'-CTCT TCATGA ATGTGGCAGCTTCTCAAC-3'

(b-13):
                                    (SEQ ID NO: 39)
5'-CTCT TCATGA TTAGATCTTGGCCGGAGC-3'
```

Primers (a-13) and (b-13) each have a BspHI restriction enzyme site added thereto.

Cloning of Valine-Producing Gene Derived from *Lysinibacillus sphaericus*

A DNA fragment comprising the leudh gene which encodes leucine dehydrogenase derived from *Lysinibacillus sphaericus* was amplified by the PCR method as described below.

In the PCR, the following set of primers was synthesized based on SEQ ID NO: 40 (the leudh gene of *Lysinibacillus sphaericus*) with the use of "394 DNA/RNA Synthesizer" made by Applied Biosystems for cloning of the leudh gene, and was used. Primers for leudh gene amplification

```
(a-14);
                                    (SEQ ID NO: 41)
5'-ACG CCCGGG AGGAGGTACGGATGGAAATCTTCAAGTATAT-3'

(b-14);
                                    (SEQ ID NO: 42)
5'-TCGG CCCGGG GAGCTC TTAACGGCCGTTCAAAATATTTTT-3'
```

Primer (a-14) has a SmaI restriction enzyme site added thereto, and primer (b-14) has SmaI and SacI restriction enzyme sites added thereto.

As the template DNA for *Corynebacterium glutamicum*, the chromosomal DNA extracted from *Corynebacterium glutamicum* R and the *Corynebacterium glutamicum* mutant having high valine productivity were used. For *Lysinibacillus sphaericus*, the chromosomal DNA extracted from *Lysinibacillus sphaericus* NBRC3525 obtained from NITE Biological Resource Center (NBRC) was used.

Actual PCR was performed with the use of a Veriti thermal cycler (made by Applied Biosystems) and PrimeSTAR HS DNA Polymerase (made by Takara Bio, Inc.) as a reaction reagent under the conditions described below.

Reaction Mixture:

| | |
|---|---|
| PrimeSTAR HS DNA Polymerase ™ (2.5 U/µL) | 0.5 µL |
| 5 X PrimeSTAR Buffer (Mg$^{2+}$ plus) | 10 µL |
| dNTP Mixture (2.5 mM each) | 4 µL |
| Template DNA | 5 µL (DNA content: 1 µg or less) |
| The above 2 primers*$^)$ | 0.5 µL each (final conc.: 1 µM) |
| Sterile distilled water | 29.5 µL |

The above ingredients were mixed, and 50 µL of the reaction mixture was subjected to PCR.
*$^)$For amplification of the ilvBN gene of *Corynebacterium glutamicum*, a combination of primers (a-9) and (b-9); for amplification of the ilvC gene of *Corynebacterium glutamicum*, a combination of primers (a-10) and (b-10); for amplification of the ilvD gene of *Corynebacterium glutamicum*, a combination of primers (a-11) and (b-11); for amplification of the ilvE gene of *Corynebacterium glutamicum*, a combination of primers (a-12) and (b-12); for amplification of the ilvBN gene of the *Corynebacterium glutamicum* mutant having high valine productivity, a combination of primers (a-13) and (b-13); and for amplification of the leudh gene of *Lysinibacillus sphaericus*, a combination of primers (a-14) and (b-14) were used.

PCR Cycle:
Denaturation step: 94° C., 60 seconds
Annealing step: 52° C., 60 seconds
Extension step: 72° C.

| | |
|---|---|
| *Corynebacterium glutamicum* ilvBN gene | 143 seconds |
| *Corynebacterium glutamicum* ilvC gene | 61 seconds |
| *Corynebacterium glutamicum* ilvD gene | 118 seconds |
| *Corynebacterium glutamicum* ilvE gene | 76 seconds |
| *Corynebacterium glutamicum* mutant having high valine productivity ilvBN gene | 143 seconds |
| *Lysinibacillus sphaericus* leudh gene | 66 seconds |

A cycle consisting of the above 3 steps was repeated 30 times.

With the use of 10 µL of the reaction mixture produced above, 0.8% agarose gel electrophoresis was performed. As a result, detected were an about 2.4-kb DNA fragment in the case of the *Corynebacterium glutamicum* ilvBN gene, an about 1.0-kb DNA fragment in the case of the *Corynebacterium glutamicum* ilvC gene, an about 2.0-kb DNA fragment in the case of the *Corynebacterium glutamicum* ilvD gene, an about 1.3-kb DNA fragment in the case of the *Corynebacterium glutamicum* ilvE gene, an about 2.4-kb DNA fragment in the case of the *Corynebacterium glutamicum* mutant having high valine productivity ilvBN gene, and an about 1.1-kb DNA fragment in the case of the *Lysinibacillus sphaericus* leudh gene.

(4) Construction of Valine-Producing Gene Expression Plasmids

Cloning of Valine-Producing Genes to pCRB207

10 µL of the about 2.4-kb DNA fragment comprising the mutated ilvBN gene derived from *Corynebacterium glutamicum* and 10 µL of the about 1.0-kb DNA fragment comprising the ilvC gene derived from *Corynebacterium glutamicum*, both of which were amplified by the PCR in the above (3), were cut with the use of restriction enzymes BspHI and NcoI, respectively, and 2 µL of the cloning vector pCRB207 comprising a promoter PgapA was cut with the use of restriction enzyme NcoI. After being processed at 70° C. for 10 minutes for deactivation of the restriction enzyme, the three kinds were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. This was named Ligation Liquid F.

Further, 10 µL of the about 2.4-kb DNA fragment comprising the mutated ilvBN gene derived from the *Corynebacterium glutamicum* having high valine productivity and 10 µL of the about 1.0-kb DNA fragment comprising the ilvC gene derived from *Corynebacterium glutamicum*, both of which were amplified by the PCR in the above (3), were cut with the use of restriction enzymes BspHI and NcoI, respectively, and 2 µL of the cloning vector pCRB207 comprising a promoter PgapA was cut with the use of restriction enzyme NcoI. After being processed at 70° C. for 10 minutes for deactivation of the restriction enzyme, the three kinds were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. This was named Ligation Liquid G.

With the separate use of the Ligation Liquids F and G, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture medium and cut with the use of the restriction enzyme to confirm the inserted fragment. As a result, in addition to an about 5.1-kb DNA fragment of the plasmid pCRB207, confirmed were an about 3.4-kb inserted fragment in the case of the ilvBN gene and the ilvC gene derived from *Corynebacterium glutamicum* (Ligation Liquid F), and an about 3.4-kb inserted fragment in the case of the mutated ilvBN gene derived from the *Corynebacterium glutamicum* having high valine productivity and the ilvC gene derived from *Corynebacterium glutamicum* (Ligation Liquid G).

The plasmid comprising the ilvBNC gene derived from *Corynebacterium glutamicum* was named pCRB207-ilvBNC/CG and the plasmid comprising the mutated ilvBNC gene derived from the *Corynebacterium glutamicum* having high valine productivity was named pCRB207-ilvBN$^{GE}$C/CG.

Cloning of Valine-Producing Genes to pCRB21

The above-mentioned plasmids pCRB207-ilvBNC/CG and pCRB207-ilvBN$^{GE}$C/CG were each cut with the use of restriction enzyme BamHI. In each case, after agarose gel electrophoresis, an about 4.4-kb DNA fragment recovered from the agarose gel with the use of QIAquick Gel Extraction Kit (made by QIAGEN), in which fragment a gapA promoter, the ilvBNC gene derived from *Corynebacterium glutamicum*, and a terminator sequence were ligated; and a DNA fragment obtained from an about 3.7-kb cloning vector pCRB21 cut with the use of BamHI and processed at 70° C. for 10 minutes for deactivation of the restriction enzyme were mixed. To the mixture, 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation. The resulting liquid was named Ligation Liquid H or I.

With the separate use of the Ligation Liquids H and I, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of chloramphenicol.

A growing strain on the culture medium was subjected to liquid culture in the usual manner. Plasmid DNA was extracted from the culture and cut with the use of restriction enzyme BamHI to confirm the inserted fragment. As a result, in addition to an about 3.7-kb DNA fragment of the plasmid pCRB21, confirmed were an about 4.4-kb inserted fragment in the case of the ilvBNC gene derived from *Corynebacterium glutamicum* (Ligation Liquid H), and an about 3.4-kb inserted fragment in the case of the mutated ilvBN gene derived from the *Corynebacterium glutamicum* having high valine productivity and the ilvC gene derived from *Corynebacterium glutamicum* (Ligation Liquid I).

The plasmid comprising the ilvBNC gene derived from *Corynebacterium glutamicum* was named pCRB-BNC and the plasmid comprising the mutated ilvBNC gene derived from the *Corynebacterium glutamicum* having high valine productivity was named pCRB-BN$^{GE}$C (FIG. 1).

Cloning of Valine-Producing Gene to pKK223-3

10 µL of the about 2.0-kb DNA fragment comprising the ilvD gene derived from *Corynebacterium glutamicum*, 10 µL of the about 1.3-kb DNA fragment comprising the ilvE gene derived from *Corynebacterium glutamicum*, or 10 µL of the about 1.1-kb DNA fragment comprising the leudh gene derived from *Lysinibacillus sphaericus*, each of which fragments was amplified by the PCR in the above (3), and 2 µL of the cloning vector pKK223-3 (made by Pharmacia) comprising a tac promoter were each cut with the use of restriction enzyme SmaI and then processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. The resulting liquid was named Ligation Liquid N, O or P.

With the use of each of the Ligation Liquids N, O and P, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of ampicillin.

A growing strain on the culture medium was subjected to liquid culture in the usual manner. Plasmid DNA was extracted from the culture medium and cut with the use of the restriction enzyme to confirm the inserted fragment. As a result, in addition to an about 4.6-kb DNA fragment of the plasmid pKK223-3, confirmed were an about 2.0-kb inserted fragment in the case of the ilvD gene derived from *Corynebacterium glutamicum* (Ligation Liquid N), an about 1.3-kb inserted fragment in the case of the ilvE gene derived from *Corynebacterium glutamicum* (Ligation Liquid O), and an about 1.1-kb inserted fragment in the case of the leudh gene derived from *Lysinibacillus sphaericus* (Ligation Liquid P).

The plasmid comprising the ilvD gene derived from *Corynebacterium glutamicum* was named pKK223-3-ilvD/CG, the plasmid comprising the ilvE gene derived from *Corynebacterium glutamicum* was named pKK223-3-ilvE/CG, and the plasmid comprising the leudh gene derived from *Lysinibacillus sphaericus* was named pKK223-3-leudh/LS.

Cloning of Valine-Producing Gene to pCRB12

From the above plasmid pKK223-3-ilvD/CG, a DNA fragment comprising the tac promoter and the ilvD gene derived from *Corynebacterium glutamicum* was amplified by the PCR method as described below.

In the PCR, the following set of primers was synthesized based on the tac promoter and the ilvD gene derived from *Corynebacterium glutamicum* (SEQ ID NO:43 (Ptac-ilvD sequence)), and was used.

Primers for Ptac-ilvD Gene Amplification (a-17);
(SEQ ID NO: 44)
5'-ATAT <u>CCTGCAGGCTAGC</u> GCTGTGCAGGTCGTAAATCACT-3'

(b-17);
(SEQ ID NO: 45)
5'-ATAT <u>GCTAGC</u> T <u>CCTGCAGG</u> TATTTGCAACGGGGAGCTC-3'

Primer (a-17) has Sse8387I and NheI restriction enzyme sites added thereto, and primer (b-17) has NheI and Sse8387I restriction enzyme sites added thereto.

As the template DNA, the above-mentioned plasmid pKK223-3-ilvD/CG was used.

Actual PCR was performed with the use of a Veriti thermal cycler (made by Applied Biosystems) and PrimeSTAR HS DNA Polymerase (made by Takara Bio, Inc.) as a reaction reagent under the conditions described below.

Reaction Mixture:

| | |
|---|---|
| PrimeSTAR HS DNA Polymerase™ (2.5 U/µL) | 0.5 µL |
| 5× PrimeSTAR Buffer (Mg$^{2+}$ plus) | 10 µL |
| dNTP Mixture (2.5 mM each) | 4 µL |
| Template DNA | 5 µL (DNA content: 1 µg or less) |
| The above 2 primers*) | 0.5 µL each (final conc.: 1 µM) |
| Sterile distilled water | 29.5 µL |

The above ingredients were mixed, and 50 µL of the reaction mixture was subjected to PCR.
*)For amplification of the Ptac-ilvD/CG sequence, a combination of primers (a-17) and (b-17) was used.

PCR Cycle:
Denaturation step: 94° C., 60 seconds
Annealing step: 52° C., 60 seconds
Extension step: 72° C., 130 seconds
A cycle consisting of the above 3 steps was repeated 30 times.

Using 10 µL of the above-produced reaction mixture, 0.8% agarose gel electrophoresis was performed, and an about 2.2-kb DNA fragment of the Ptac-ilvD/CG sequence was detected.

10 µL of the about 2.2-kb DNA fragment amplified by the above PCR, the fragment comprising the tac promoter sequence and the ilvD sequence derived from *Corynebacterium glutamicum*, and 2 µL of cloning vector pCRB12 were each cut with the use of restriction enzyme Sse8387I and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. This was named Ligation Liquid Q.

With the use of the Ligation Liquid Q, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture medium and cut with the use of restriction enzyme Sse8387I to confirm the inserted fragment. As a result, in addition to an about 3.7-kb DNA fragment of the cloning vector pCRB12, an about 2.2-kb DNA fragment of the Ptac-ilvD/CG sequence (Ligation Liquid Q) was confirmed.

The plasmid comprising the ilvD gene derived from *Corynebacterium glutamicum* was named pCRB12-ilvD/CG.

From the above plasmids pKK223-3-ilvE/CG and pKK223-3-leudh/LS, a DNA fragment comprising the tac promoter and the ilvE gene derived from *Corynebacterium glutamicum* and a DNA fragment comprising the tac promoter and the-leudh gene derived from *Lysinibacillus sphaericus* were respectively amplified by the PCR method as described below.

In the PCR, the following sets of primers were synthesized based on the tac promoter-fused ilvE gene derived from *Corynebacterium glutamicum* (SEQ ID NO: 46 (Ptac-ilvE sequence)) and the tac promoter-fused leudh gene derived from *Lysinibacillus sphaericus* (SEQ ID NO: 47 (Ptac-leudh sequence)), and were used.

Primers for Ptac-ilvE Gene Amplification

```
(a-18);
                                    (SEQ ID NO: 48)
5'-ATAT GCTAGC T CCTGCAGG CTGTGCAGGTCGTAAATCAC-3'

(b-18);
                                    (SEQ ID NO: 49)
5'-ATAT CCTGCAGGCTAGC ATCCCTGACTCCACCCCCTAC-3'
```

Primer (a-18) has NheI and Sse8387I restriction enzyme sites added thereto, and primer (b-18) has Sse8387I and NheI restriction enzyme sites added thereto.

Primers for Ptac-leudh Gene Amplification

```
(a-19);
                                    (SEQ ID NO: 50)
5'-ATAT GCTAGC T CCTGCAGG CTGTGCAGGTCGTAAATCAC-3'

(b-19);
                                    (SEQ ID NO: 51)
5'-ATGC CCTGCAGGCTAGC GTTAACGGCCGTTCAAAATAT-3'
```

Primer (a-19) has NheI and Sse8387I restriction enzyme sites added thereto, and primer (b-19) has Sse8387I and NheI restriction enzyme sites added thereto.

As the template DNA, the above-mentioned plasmid pKK223-3-ilvE/CG and pKK223-3-leudh/LS were used.

Actual PCR was performed with the use of a Veriti thermal cycler (made by Applied Biosystems) and PrimeSTAR HS DNA Polymerase (made by Takara Bio, Inc.) as a reaction reagent under the conditions described below.

Reaction Mixture:

| | |
|---|---|
| PrimeSTAR HS DNA Polymerase ™ (2.5 U/μL) | 0.5 μL |
| 5 X PrimeSTAR Buffer (Mg$^{2+}$ plus) | 10 μL |
| dNTP Mixture (2.5 mM each) | 4 μL |
| Template DNA | 5 μL (DNA content: 1 μg or less) |
| The above 2 primers*) | 0.5 μL each (final conc.: 1 μM) |
| Sterile distilled water | 29.5 μL |

The above ingredients were mixed, and 50 μL of the reaction mixture was subjected to PCR.
*)For amplification of the Ptac-ilvE/CG sequence, a combination of primers (a-18) and (b-18), and for amplification of the Ptac-leudh/LS sequence, a combination of primers (a-19) and (b-19) were used.

PCR Cycle:
Denaturation step: 94° C., 60 seconds
Annealing step: 52° C., 60 seconds
Extension step: 72° C.
Ptac-ilvE/CG, 90 seconds
Ptac-leudh/LS, 80 seconds A cycle consisting of the above 3 steps was repeated 30 times.

Using 10 μL of the above-produced reaction mixture, 0.8% agarose gel electrophoresis was performed, and an about 1.5-kb fragment of the Ptac-ilvE/CG sequence and an about 1.3-kb DNA fragment of the Ptac-leudh/LS sequence were detected.

10 μL of the about 1.5-kb DNA fragment comprising the tac promoter-fused ilvE sequence derived from *Corynebacterium glutamicum* or the 10 μL of the about 1.3-kb DNA fragment comprising the tac promoter-fused leudh sequence derived from *Lysinibacillus sphaericus*, each of which was amplified by the above PCR, and 2 μL of the pCRB12-ilvD/CG comprising the tac promoter-fused ilvD sequence derived from *Corynebacterium glutamicum* were each cut with the use of restriction enzyme NheI and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. The resulting liquid was named Ligation Liquid R or S.

With the separate use of the Ligation Liquids R and S, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme NheI to confirm the inserted fragment. As a result, in addition to an about 5.9-kb DNA fragment of the plasmid pCRB12-ilvD/CG comprising the tac promoter-fused ilvD sequence derived from *Corynebacterium glutamicum*, confirmed were an about 1.5-kb DNA fragment in the case of the Ptac-ilvE sequence (Ligation Liquid R) and an about 1.3-kb DNA fragment in the case of the Ptac-leudh sequence (Ligation Liquid S).

Figure 2:
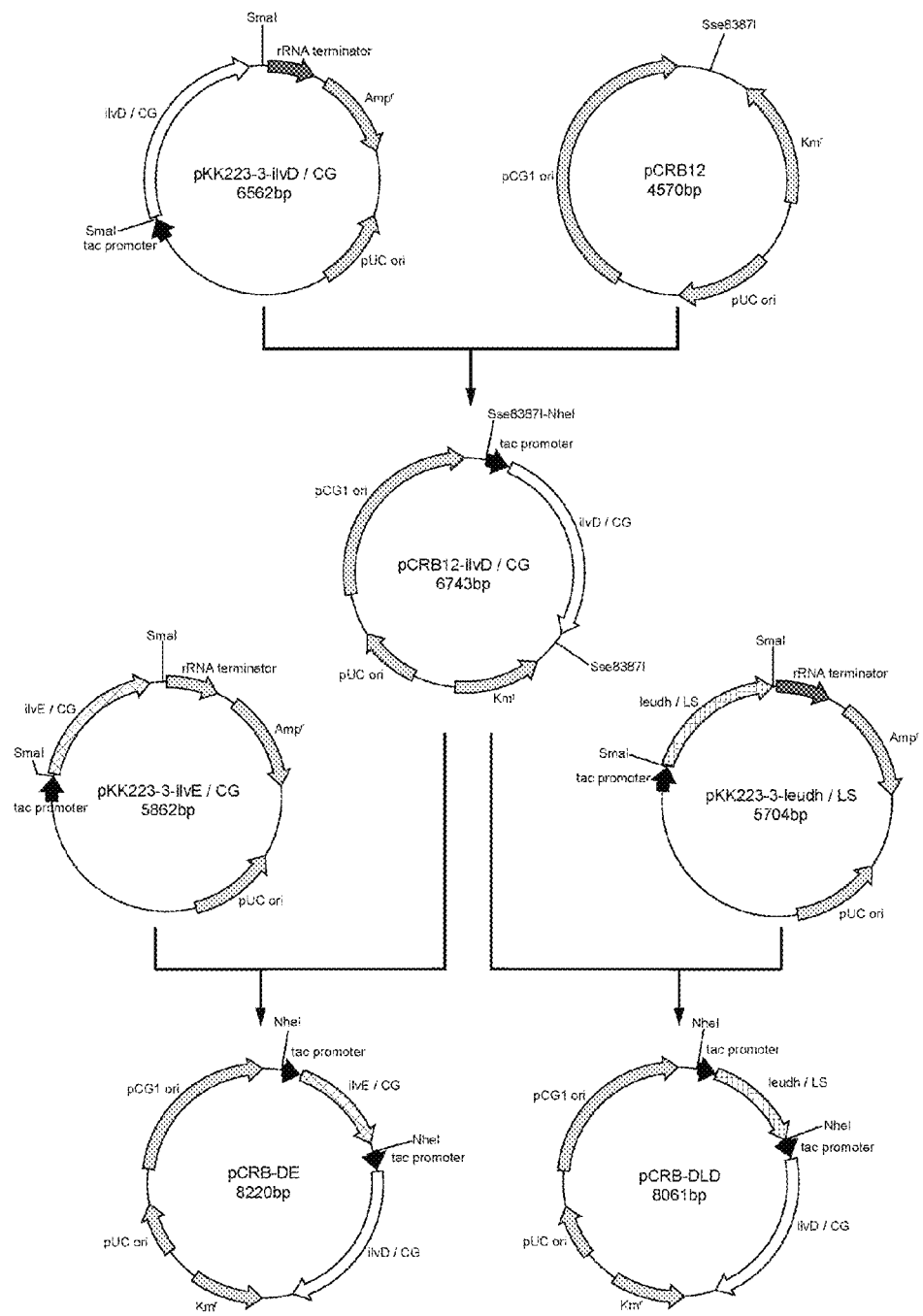
FIG. 2 shows the constructs of vectors used in Examples.

The plasmid comprising the ilvD gene and the ilvE gene derived from *Corynebacterium glutamicum* was named pCRB-DE. The plasmid comprising the ilvD gene derived from *Corynebacterium glutamicum* and the leudh gene derived from *Lysinibacillus sphaericus* was named pCRB-DLD (FIG. 2).

(5) Site-Directed Mutagenesis in Valine-Producing Gene Using PCR

In order to introduce a mutation for improved valine productivity into an ilvC gene which encodes acetohydroxy acid isomeroreductase derived from *Corynebacterium glutamicum*, a DNA fragment comprising the ilvBNC sequence derived from *Corynebacterium glutamicum* and a DNA fragment comprising the ilvBNC sequence derived from the *Corynebacterium glutamicum* having high valine productivity were amplified by the PCR method as described below.

In the PCR, the following sets of primers were synthesized based on the SEQ ID NO: 52 (ilvC gene) for cloning of the plasmid pCRB-BNC comprising the ilvBNC sequence derived from *Corynebacterium glutamicum* and the plasmid pCRB-BN$^{GE}$C comprising the ilvBNC sequence derived from the *Corynebacterium glutamicum* having high valine productivity, and were used.

Primers for ilvC (S34G) Mutagenesis

```
(a-15);
                                    (SEQ ID NO: 53)
5'-CGCACACGGCCAGAACC-3'

(b-15);
                                    (SEQ ID NO: 54)
5'-GGTTCTGGCCGTGTGCG-3'
```

The underlined bases are the ones for mutagenesis.

Primers for ilvC (L48E, R49F) Mutagenesis

```
(a-16);
                                    (SEQ ID NO: 55)
5'-CATTGGTGAGTTCGAGGGC-3'

(b-16);
                                    (SEQ ID NO: 56)
5'-GCCCTCGAACTCACCAATG-3'
```

The underlined bases are the ones for mutagenesis.

(5)-1 ilvC (S34G) Mutagenesis

As the template DNA, the plasmid pCRB-BNC comprising the ilvBNC sequence derived from *Corynebacterium glutamicum* and the plasmid pCRB-BN$^{GE}$C comprising the ilvBNC sequence derived from the *Corynebacterium glutamicum* having high valine productivity were used.

Actual PCR was performed with the use of a Veriti thermal cycler (made by Applied Biosystems) and PrimeSTAR HS DNA Polymerase (made by Takara Bio, Inc.) as a reaction reagent under the conditions described below.

Reaction Mixture:

| | |
|---|---|
| PrimeSTAR HS DNA Polymerase ™ (2.5 U/μL) | 0.5 μL |
| 5 X PrimeSTAR Buffer (Mg$^{2+}$ plus) | 10 μL |
| dNTP Mixture (2.5 mM each) | 4 μL |
| Template DNA | 5 μL (DNA content: 1 μg or less) |
| The above 2 primers*) | 0.5 μL each (final conc.: 1 μM) |
| Sterile distilled water | 29.5 μL |

The above ingredients were mixed, and 50 μL of the reaction mixture was subjected to PCR.
*)For amplification of the pCRB-BNC sequence and the pCRB-BN$^{GE}$C sequence, a combination of primers (a-15) and (b-15) was used.

PCR Cycle:
  Denaturation step: 94° C., 60 seconds
  Annealing step: 52° C., 60 seconds
  Extension step: 72° C.
  pCRB-BNC, 486 seconds
  pCRB-BN$^{GE}$C, 486 seconds
  A cycle consisting of the above 3 steps was repeated 30 times.

Using 10 μL of the above-produced reaction mixture, 0.8% agarose gel electrophoresis was performed, and an about 8.1-kb fragment comprising the pCRB-BNC sequence and an about 8.1-kb DNA fragment comprising the pCRB-BN$^{GE}$C sequence were detected.

To 10 μL of the about 8.1-kb DNA fragment comprising the pCRB-BNC or 10 μL of the about 8.1-kb DNA fragment comprising the pCRB-BN$^{GE}$C, each of which was amplified by the above PCR, 1 μL of T4 DNA ligase 10× buffer solution and 1 unit of T4 DNA ligase (made by Takara SHUZO) were added. Sterile distilled water was added thereto so that the total volume was 10 μL, and the mixture was allowed to react at 15° C. for 3 hours for ligation. The resulting liquid was named Ligation Liquid J or K.

With the separate use of the Ligation Liquids J and K, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of chloramphenicol.

A growing strain on the culture medium was subjected to liquid culture in the usual manner. Plasmid DNA was extracted from the culture, and the insertion of the mutation site was confirmed by the sequence analysis of the plasmid.

The plasmid comprising an ilvC gene which encodes acetohydroxy acid isomeroreductase derived from *Corynebacterium glutamicum* and which has a mutation changing the serine at position 34 to glycine was named pCRB-BNC$^{SM}$ or pCRB-BN$^{GE}$C$^{SM}$.

(5)-2 ilvC (L48E, R49F) Mutagenesis

As the template DNA, the pCRB-BNC$^{SM}$ and pCRB-BN$^{GE}$C$^{SM}$ constructed in the above "(5)-1 ilvC(S34G) mutagenesis" were used.

Actual PCR was performed with the use of a Veriti thermal cycler (made by Applied Biosystems) and PrimeSTAR HS DNA Polymerase (made by Takara Bio, Inc.) as a reaction reagent under the conditions described below.

Reaction Mixture:

| | |
|---|---|
| PrimeSTAR HS DNA Polymerase ™ (2.5 U/μL) | 0.5 μL |
| 5 X PrimeSTAR Buffer (Mg$^{2+}$ plus) | 10 μL |
| dNTP Mixture (2.5 mM each) | 4 μL |
| Template DNA | 5 μL (DNA content: 1 μg or less) |
| The above 2 primers*) | 0.5 μL each (final conc.: 1 μM) |
| Sterile distilled water | 29.5 μL |

The above ingredients were mixed, and 50 μL of the reaction mixture was subjected to PCR.
*)For amplification of the pCRB-BNC$^{SM}$ sequence and the pCRB-BN$^{GE}$C$^{SM}$ sequence, a combination of primers (a-16) and (b-16) was used.

PCR Cycle:
  Denaturation step: 94° C., 60 seconds
  Annealing step: 52° C., 60 seconds
  Extension step: 72° C.
  pCRB-BNC$^{SM}$, 486 seconds
  pCRB-BN$^{GE}$C$^{SM}$, 486 seconds
  A cycle consisting of the above 3 steps was repeated 30 times.

Using 10 μL of the above-produced reaction mixture, 0.8% agarose gel electrophoresis was performed, and an about 8.1-kb fragment comprising the pCRB-BNC$^{SM}$ sequence and an about 8.1-kb DNA fragment comprising the pCRB-BN$^{GE}$C$^{SM}$ sequence were detected.

To 10 μL of the about 8.1-kb DNA fragment comprising the pCRB-BNC$^{SM}$ or 10 μL of the about 8.1-kb DNA fragment comprising the pCRB-BN$^{GE}$C$^{SM}$, each of which was amplified by the above PCR, 1 μL of T4 DNA ligase 10× buffer solution and 1 unit of T4 DNA ligase (made by Takara SHUZO) were added. Sterile distilled water was added thereto so that the total volume was 10 μL, and the mixture was allowed to react at 15° C. for 3 hours for ligation. The resulting liquid was named Ligation Liquid L or M.

With the separate use of the Ligation Liquids L and M, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of chloramphenicol.

A growing strain on the culture medium was subjected to liquid culture in the usual manner. Plasmid DNA was extracted from the culture, and the insertion of the mutation site was confirmed by the sequence analysis of the plasmid.

The plasmid comprising an ilvC gene which encodes acetohydroxy acid isomeroreductase derived from *Corynebacterium glutamicum* and which has mutations changing the serine at position 34 to glycine, the leucine at position 48 to glutamic acid, and the arginine at position 49 to phenylalanine was named pCRB-BNC$^{TM}$ or pCRB-BN$^{GE}$C$^{TM}$ (FIG. 1).

(6) Construction of Transgenic Strains for Valine-Producing Gene

With the use of the above-described plasmids pCRB-BNC and pCRB-DE, transformation of a *Corynebacterium glutamicum* R ldhA mutant [J. Mol. Biotechnol., Vol. 8, 243-254 (2004)] was performed by electroporation (Agric. Biol. Chem., Vol. 54, 443-447 (1990) and Res. Microbial., Vol. 144, 181-185 (1993)), and the strain was applied to A agar medium containing 50 μg/mL of kanamycin and 5 μg/mL of chloramphenicol.

A growing strain on the culture medium was subjected to liquid culture in the usual manner. Plasmid DNA was extracted from the culture and cut with the use of restriction enzymes to confirm the inserted plasmids. As a result, transfection of the above-constructed plasmids pCRB-BNC and pCRB-DE was confirmed.

The obtained strain was named *Corynebacterium glutamicum* VAL1.

With the use of the above-described plasmids pCRB-BNC$^{TM}$ and pCRB-DE, transformation of a *Corynebacterium glutamicum* R ldhA mutant [J. Mol. Biotechnol., Vol. 8, 243-254 (2004)] was performed by electroporation (Agric. Biol. Chem., Vol. 54, 443-447 (1990) and Res. Microbiol., Vol. 144, 181-185 (1993)), and the strain was applied to A agar medium containing 50 μg/mL of kanamycin and 5 μg/mL of chloramphenicol.

A growing strain on the culture medium was subjected to liquid culture in the usual manner. Plasmid DNA was extracted from the culture and cut with the use of restriction enzymes to confirm the inserted plasmids. As a result, transfection of the above-constructed plasmids pCRB-BNC$^{TM}$ and pCRB-DE was confirmed.

The obtained strain was named *Corynebacterium glutamicum* VAL2.

With the use of the above-described plasmids pCRB-BNC$^{TM}$ and pCRB-DLD, transformation of a *Corynebacterium glutamicum* R ldhA mutant [J. Mol. Biotechnol., Vol. 8, 243-254 (2004)] was performed by electroporation (Agric. Biol. Chem., Vol. 54, 443-447 (1990) and Res. Microbiol., Vol. 144, 181-185 (1993)), and the strain was applied to A agar medium containing 50 μg/mL of kanamycin and 5 μg/mL of chloramphenicol.

A growing strain on the culture medium was subjected to liquid culture in the usual manner. Plasmid DNA was extracted from the culture and cut with the use of restriction enzymes to confirm the inserted plasmids. As a result, transfection of the above-constructed plasmids pCRB-BNC$^{TM}$ and pCRB-DLD was confirmed.

The obtained strain was named *Corynebacterium glutamicum* VAL3.

With the use of the above-described plasmids pCRB-BN$^{GE}$C$^{TM}$ and pCRB-DLD, transformation of a *Corynebacterium glutamicum* R ldhA mutant [J. Mol. Biotechnol., Vol. 8, 243-254 (2004)] was performed by electroporation (Agric. Biol. Chem., Vol. 54, 443-447 (1990) and Res. Microbiol., Vol. 144, 181-185 (1993)), and the strain was applied to A agar medium containing 50 μg/mL of kanamycin and 5 μg/mL of chloramphenicol.

A growing strain on the culture medium was subjected to liquid culture in the usual manner. Plasmid DNA was extracted from the culture and cut with the use of restriction enzymes to confirm the inserted plasmids. As a result, transfection of the above-constructed plasmids pCRB-BN$^{GE}$C$^{TM}$ and pCRB-DLD was confirmed.

The obtained strain was named *Corynebacterium glutamicum* VAL4.

The outline of gene recombination in the above-obtained strains is shown in Table 2.

*Corynebacterium glutamicum* VAL4 was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-1122 on Aug. 11, 2011.

TABLE 2

Valine-producing gene transgenic strains

| Strain | Host strain | Transfected gene (gene name/origin) | | |
|---|---|---|---|---|
| VAL1 | *Corynebacterium* | ilvBNC/CG | ilvD/CG | ilvE/CG |
| VAL2 | *glutamicum* R | ilvBNC ™/CG | ilvD/CG | ilvE/CG |
| VAL3 | ΔldhA | ilvBNC ™/CG | ilvD/CG | Leudh/LS |
| VAL4 | | ilvBN$^{GE}$C ™/CG | ilvD/CG | Leudh/LS |

*) Abbreviations in the table stand for the following.
<Abbreviation for gene origin>
CG; *Corynebacterium glutamicum*
LS; *Lysinibacillus sphaericus*
ΔldhA; lactase dehydrogenase gene disruptant
ilvBNC; wild-type acetohydroxy acid synthase gene and wild-type acetohydroxy acid isomeroreductase gene
ilvBNC ™; wild-type acetohydroxy acid synthase gene and mutated acetohydroxy acid isomeroreductase gene (S34G, L48E, R49F)
ilvBN$^{GE}$C ™; mutated acetohydroxy acid synthase gene (G156E) and mutated acetohydroxy acid isomeroreductase gene (S34G, L48E, R49F)
ilvD; wild-type dihydroxy acid dehydratase gene
ilvE; wild-type transaminase gene
leudh; wild-type leucine dehydrogenase gene Example 3

Experiment of Valine Production Using *Corynebacterium glutamicum* Valine-Producing Gene Transgenic Strains For comparison of valine production among various combinations of introduced genes, namely, the *Corynebacterium glutamicum* ilvBN gene or the highly valine-producing mutated *Corynebacterium glutamicum* gene ilvBN$^{GE}$, each of which encodes acetohydroxy acid synthase; the *Corynebacterium glutamicum* ilvC gene or the highly valine-producing mutated *Corynebacterium glutamicum* gene ilvC$^{TM}$, each of which encodes acetohydroxy acid isomeroreductase; the *Corynebacterium glutamicum* ilvD gene which encodes dihydroxy acid dehydratase; and the *Corynebacterium glutamicum* ilvE gene which encodes transaminase, or the *Lysinibacillus sphaericus* leudh gene which encodes leucine dehydrogenase, various combinations of the genes were introduced into a *Corynebacterium glutamicum* R ldhA mutant as shown in Example 2.

Each of the valine-producing strains shown in Example 2 (Table 2) was applied to A agar medium (2 g of (NH$_2$)$_2$CO$_3$ 7 g of (NH$_4$)$_2$SO$_4$, 0.5 g of KH$_2$PO$_4$, 0.5 g of K$_2$HPO$_4$, 0.5 g of MgSO$_4$.7H$_2$O, 1 mL of 0.06% (w/v) Fe$_2$SO$_4$.7H$_2$O+0.042% (w/v) MnSO$_4$.2H$_2$O, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing 50 μg/mL of kanamycin and 5 μg/mL of chloramphenicol, and left stand in the dark at 28° C. for 20 hours.

An inoculation loop of each of the *Corynebacterium glutamicum* valine-producing gene transgenic strains grown on a plate as above was inoculated into a test tube containing 10 mL of A liquid medium (2 g of (NH$_2$)$_2$CO$_3$ 7 g of (NH$_4$)$_2$SO$_4$, 0.5 g of KH$_2$PO$_4$, 0.5 g of K$_2$HPO$_4$, 0.5 g of MgSO$_4$.7H$_2$O, 1 mL of 0.06% (w/v) Fe$_2$SO$_4$.7H$_2$O+0.042% (w/v) MnSO$_4$.2H$_2$O, 1 mL of 0.02% (w/v) biotin solution, 2 mL of 0.01% (w/v) thiamin solution, 2 g of yeast extract, 7 g of vitamin assay casamino acid, and 40 g of glucose were dissolved in 1 L of distilled water) containing the antibiotics, and aerobically cultured with shaking at 28° C. for 15 hours.

<Aerobic Culture>

The *Corynebacterium glutamicum* valine-producing strain grown in the above conditions was inoculated in a 2-L conical flask containing 500 mL of A liquid medium containing 50 µg/mL of kanamycin, 5 µg/mL of chloramphenicol, and 25 µg/mL of zeocin, and aerobically cultured with shaking at 28° C. for 15 hours.

<Valine Production Under Reducing Conditions>

The bacterial cells of the strain cultured and proliferated as above were collected by centrifugation (5,000×g at 4° C. for 15 minutes). The obtained bacterial cells were suspended in BT (-urea) liquid medium (0.7% ammonium sulfate, 0.05% potassium dihydrogen phosphate, 0.05% dipotassium hydrogen phosphate, 0.05% magnesium sulfate heptahydrate, 0.0006% iron sulfate heptahydrate, 0.00042% manganese sulfate hydrate, 0.00002% biotin and 0.00002% thiamine hydrochloride) so that the concentration of the bacterial cell was 40 g (cell dry weight)/L. To a 100-mL medium bottle, 60 mL of the cell suspension was transferred, glucose was added so as to be 8% in concentration, and the reaction was allowed to proceed under reducing conditions (the ORP of the reaction mixture: −450 mV) in a water bath at 33° C. with stirring. During the reaction, the pH of the reaction mixture was kept at or above 7.0 through addition of 2.5 N aqueous ammonia controlled by a pH controller (Type: DT-1023 made by Able).

After 24 hours, the reaction mixture was sampled and then centrifuged (15,000×g at 4° C. for 10 minutes), and the obtained supernatant was used for quantitative determination of valine.

The results are shown in Table 3.

The *Corynebacterium glutamicum* ΔldhA strain not having any valine-producing gene expression plasmids introduced thereinto produced 5.37 mM of valine, and the VAL1 strain produced 53.9 mM of valine. That is, high expression of the ilVBNCDE genes increased the amount of produced valine about 10-fold.

Compared to the VAL1 strain, the VAL2 strain produced 239 mM of valine. That is, high expression of the mutated gene ilVC$^{TM}$ introduced instead of the wild-type gene ilvC further increased the amount of produced valine about 4.4-fold.

Compared to the VAL2 strain, the VAL3 strain produced 1170 mM of valine. That is, high expression of the leudh gene introduced instead of the ilvE gene further increased the amount of produced valine about 4.9-fold.

Compared to the VAL3 strain, the VAL4 strain produced 1470 mM of valine. That is, high expression of the mutated gene ilVBN$^{GE}$ introduced instead of the wild-type gene ilvBN further increased the amount of produced valine about 1.3-fold.

TABLE 3

Experiment of valine production using valine-producing gene transgenic strains

| Strain | Transfected gene (gene name/origin) | | | Amount of valine production (mM) |
|---|---|---|---|---|
| ΔldhA | | | | 5.4 |
| VAL1 | ilvBNC/CG | ilvD/CG | ilvE/CG | 53.9 |
| VAL2 | ilvBNC $^{TM}$/CG | ilvD/CG | ilvE/CG | 239 |
| VAL3 | ilvBNC $^{TM}$/CG | ilvD/CG | Leudh/LS | 1170 |
| VAL4 | ilvBN$^{GE}$C $^{TM}$/CG | ilvD/CG | Leudh/LS | 1470 |

*) Abbreviations in the table are the same as those in Table 2.

INDUSTRIAL APPLICABILITY

According to the process of the present invention, valine can be produced with a practical efficiency using microorganisms.

The invention claimed is:

1. A transformant obtainable by introducing one or more of the following DNAs (a), (b), and (c) into a coryneform bacterium as a host:
   (a) A DNA consisting of the base sequence of SEQ ID NO: 37
   (b) A DNA consisting of the base sequence of SEQ ID NO: 57
   (c) A DNA consisting of the base sequence of SEQ ID NO: 40 has 90% or more of identity with the base sequence of SEQ ID NO: 40 and which encodes a polypeptide having leucine dehydrogenase activity.

2. The transformant according to claim 1, wherein a DNA consisting of the base sequence of SEQ ID NO: 43 or a DNA which has 90% or more of identity with the base sequence of SEQ ID NO: 43 and which encodes a polypeptide having dihydroxy acid dehydratase activity is also introduced thereinto.

3. The transformant according to claim 1, wherein the lactate dehydrogenase gene of the coryneform bacterium as the host is disrupted or deleted.

4. *Corynebacterium glutamicum* VAL4 (Accession Number: NITE BP-1122), which is a transformant of *Corynebacterium glutamicum*.

5. A process for producing valine, which comprises contacting the transformant of claim 1 with a culture media containing a sugar under reducing conditions, and a step of recovering valine from the reaction mixture.

6. The process according to claim 5, wherein the transformant does not grow in the reaction step.

* * * * *